(12) United States Patent
Min

(10) Patent No.: US 8,389,708 B2
(45) Date of Patent: Mar. 5, 2013

(54) METHOD OF CANCER TREATMENT USING SIRNA SILENCING

(76) Inventor: Weiping Min, London (CA)

( * ) Notice: Subject to any disclaimer, the term of this patent is extended or adjusted under 35 U.S.C. 154(b) by 465 days.

(21) Appl. No.: 11/917,593

(22) PCT Filed: Jun. 15, 2006

(86) PCT No.: PCT/CA2006/000984
§ 371 (c)(1),
(2), (4) Date: Jul. 25, 2008

(87) PCT Pub. No.: WO2006/133561
PCT Pub. Date: Dec. 21, 2006

(65) Prior Publication Data
US 2009/0220582 A1  Sep. 3, 2009

Related U.S. Application Data

(60) Provisional application No. 60/690,494, filed on Jun. 15, 2005.

(51) Int. Cl.
*C07H 21/04* (2006.01)
*C12N 15/11* (2006.01)
*C12Q 1/68* (2006.01)

(52) U.S. Cl. ....... 536/24.5; 514/44 A; 435/6.1; 536/23.1

(58) Field of Classification Search .................. None
See application file for complete search history.

(56) References Cited

U.S. PATENT DOCUMENTS

2003/0194803 A1* 10/2003 Mellor et al. ................. 435/372

FOREIGN PATENT DOCUMENTS

| CA | 2431080 A1 | 12/2004 |
|---|---|---|
| CA | 2449186 A1 | 6/2005 |
| WO | WO 03/104456 A1 | 12/2003 |
| WO | WO 2004/033620 A2 | 4/2004 |

OTHER PUBLICATIONS

Munn et al. Trends in Mol. Med., 2004; 10(1) 15-18.*
Gastman, B.R. et al. .1999 "Fas ligand is expressed on human squamous cell carcinomas of the head and neck, and it promotes apoptosis of T lymphocytes" *Cancer Research* 59:5356-5364.
Krishnakumar S. et al. 2004 "Expression of Fas ligand in retinoblastoma" *Cancer* 101:1672-1676.
Muller A.J. et al. 2005 "Inhibition of indoleamine 2, 3-dioxygenase, an immunoregulatory target of the cancer suppression gene *Bin1*, potentiates cancer chemotherapy" *Nature Medicine* 11:312-319.
Mueller A.J. et al. 2005 "Inhibition of indoleamine 2, 3-dioxygenase, an immunoregulatory target of the cancer suppression gene *Bin1*, potentiates cancer chemotherapy" *Nature Medicine* 11: (Supplemental information).
Netzer, P. et al. 2001 "Inhibition of human colon cancer cell growth by antisense oligodeoxynucleotides targeted at basic fibroblast growth factor" *Alimentary Pharmacology and Therapeutics* 15: 1673-1679.
Nückel, H. et al. 2005 "HLA-G expression is associated with unfavorable outcome and immunodeficiency in chronic lymphocytic leukemia" *Blood* 105:1694-1698.
Rao, CH.V. et al. 2004 "Human chorionic gonadotropin decreases proliferation and invasion of breast cancer MCF-7 cells by inhibiting NF-κB and AP-1 activation" *J Biol Chem* 279:25503-25510.
Spaner, D.E. et al. 2004 "Amplifying cancer vaccine responses by modifying pathogenic gene programs in tumor cells" *J Leukocyte Biol* 76:338-351.
Takei, Y. et al. 2004 "A small interfering RNA targeting vascular endothelial growth factor as cancer therapeutics" *Cancer Research* 64:3365-3370.
Yang, B.-C. et al. 2003 "Mediation of enhanced transcription of the IL-10 gene in T-cels, upon contact with human glioma cells, by Fas signaling through a protein kinase A-independent pathway" *J Immunol* 171:3947-3954.
Zhang, L. et al. 2003 "Vector-based RNAi, a novel tool for isoform-specific knock-down of VEGF and anti-angiogenesis gene therapy of cancer" *Biochem and Biophys Res Comm* 202:1169-1178.
Filleur, S. et al. 2003 "SiRNA-mediated inhibition of vascular endothelial growth factor severely limits tumor resistance to antiangiogenic thrombospondin-1 and slows tumor vascularization and growth" *Cancer Res* 63:3919-3922.
McCarthy, B. et al. 2004 "RNA Interference of IL-10 in Leukemic B-1 Cells" *Cancer Immunity* (Online) vol. 4, p. 6 Retrieved from the Internet: http://www.cancerimmunity.org/v4p6/040304.htm.

* cited by examiner

*Primary Examiner* — Doug Schultz
(74) *Attorney, Agent, or Firm* — Baumgartner Patent Law; Marc Baumgartner

(57) ABSTRACT

The present invention is a method for the treatment of cancer involving tumor derived immunosuppression in a subject. The method comprises administering to a subject one or more siRNA constructs capable of inhibiting the expression of an immunosuppressive molecule. The invention also provides siRNA constructs and compositions.

4 Claims, 10 Drawing Sheets

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Target site in IDO

<400> SEQUENCE: 1
gttctagaag gatccttga                                                19

<210> SEQ ID NO 2
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 2
gggctttgct ctaccacatc cact                                          24
```

```
<210> SEQ ID NO 3
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 3
acatcgtcat cccctcggtt cc                                              22
```

METHOD OF CANCER TREATMENT USING SIRNA SILENCING

RELATED APPLICATIONS

This application is a U.S. National Phase of International Application No. PCT/CA2006/000984, filed Jun. 15, 2006, designating the U.S. and published in English on Dec. 21, 2006 as WO 2006/133561, which claims the benefit of U.S. Provisional Application No. 60/690,494, filed Jun. 15, 2005.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is SEQ.txt, the date of creation of the ASCII text file is Jul. 26, 2011, and the size of the ASCII text file is 4 KB.

FIELD OF THE INVENTION

The invention relates to a novel method for cancer therapy. More specifically, the invention is directed to the silencing of immunosuppressive cancer causing genes using short interfering RNA (siRNA) leading to an increase in the immune response, a decrease in tumor-induced immunosuppression and a decrease in in vivo tumor progression.

BACKGROUND OF THE INVENTION

Throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure.

The ability of cancer cells to evade or escape immune detection and destruction is recognized as a key hallmark of carcinogenesis and cancer progression (Rodriguez, P. C., A. H. Zea, and A. C. Ochoa. 2003. Mechanisms of tumor evasion from the immune response. *Cancer Chemother Biol Response Modif* 21:351.). Essential to this process is the ability of tumor cells to create a state of localized immune tolerance or non-responsiveness towards their otherwise immunogenic antigens. Such immunosuppression and evasion can be achieved through a variety of mechanisms at the disposal of cancerous cells, many of which have been characterized; secretion of Th2-associated cytokines such as IL-10 or TGF-β leading towards Th2 polarization (Sheu, B. C., R. H. Lin, H. C. Lien, H. N. Ho, S. M. Hsu, and S. C. Huang. 2001. Predominant Th2/Tc2 polarity of tumor-infiltrating lymphocytes in human cervical cancer. *J Immunol* 167:2972.), over-expression of Fas-L/TRAIL 15,16, over-expression of complement inhibitors (DAF, CD55) (Murray, K. P., S. Mathure, R. Kaul, S. Khan, L. F. Carson, L. B. Twiggs, M. G. Martens, and A. Kaul. 2000. Expression of complement regulatory proteins-CD 35, CD 46, CD 55, and CD 59-in benign and malignant endometrial tissue. *Gynecol Oncol* 76:176.) 21 and over-expression of HLA-G protecting against NK-induced lysis (Ugurel, S., Reinhold, U. & Tilgen, W. HLA-G in melanoma: A new strategy to escape from immunosurveillance? *Onkologie* 25, 129-34 (2002).

An immunosuppressive enzyme in this process of malignant tolerance has been identified as indoleamine 2,3-dioxygenase (IDO), a tryptophan catabolizing enzyme (Uyttenhove, C., L. Pilotte, I. Theate, V. Stroobant, D. Colau, N. Parmentier, T. Boon, and B. J. Van den Eynde. 2003. Evidence for a tumoral immune resistance mechanism based on tryptophan degradation by indoleamine 2,3-dioxygenase. *Nat Med* 9:1269). IDO is the rate-limiting enzyme in the kynurenine pathway which converts the essential amino acid L-tryptophan to L-kynurenine. Through the degradation of tryptophan, IDO is believed to suppress T cells through two primary mechanisms: 1) through the depletion of tryptophan (tryptophan depletion theory) and 2) through the generation of toxic downstream metabolites of the kynurenine pathway (ie. quinolinic and picolinic acid) which are known to induce T cell apoptosis (tryptophan utilization theory)(Moffett, J. R., and M. A. Namboodiri. 2003. Tryptophan and the immune response. *Immunol Cell Biol* 81:247).

IDO is expressed by a variety of antigen presenting cells (APCs) including monocyte-derived macrophages, dendritic cells, and many different subsets of tumor cells both murine and human. Expression of IDO by both professional APCs (monocyte-derived macrophages, human and murine dendritic cells) and nonprofessional APCs (tumor cell lines) has been proven to inhibit locally responding T cells in vitro (Bauer, T. M., L. P. Jiga, J. J. Chuang, M. Randazzo, G. Opelz, and P. Terness. 2005. Studying the immunosuppressive role of indoleamine 2,3-dioxygenase: tryptophan metabolites suppress rat allogeneic T-cell responses in vitro and in vivo. *Transpl Int* 18:95; Mellor, A. L., D. B. Keskin, T. Johnson, P. Chandler, and D. H. Munn. 2002. Cells expressing indoleamine 2,3-dioxygenase inhibit T cell responses. *J Immunol* 168: 3771). Expression of IDO has also been implicated in the generation of tryptophan metabolites such as quinolinic acid, 3-hydroxyanthranilic acid, anthranilic acid, kynurenine, and 3-hydroxykynurenine, which are considered toxic and can induce apoptosis of locally responding T cells (Moffett, J. R., and M. A. Namboodiri. 2003. Tryptophan and the immune response. *Immunol Cell Biol* 81:247; Fallarino, F., U. Grohmann, C. Vacca, R. Bianchi, C. Orabona, A. Spreca, M. C. Fioretti, and P. Puccetti. 2002. T cell apoptosis by tryptophan catabolism. *Cell Death Differ* 9:1069; Frumento, G., R. Rotondo, M. Tonetti, G. Damonte, U. Benatti, and G. B. Ferrara. 2002. Tryptophan-derived catabolites are responsible for inhibition of T and natural killer cell proliferation induced by indoleamine 2,3-dioxygenase. *J Exp Med* 196: 459; Terness, P., T. M. Bauer, L. Rose, C. Dufter, A. Watzlik, H. Simon, and G. Opelz. 2002. Inhibition of allogeneic T cell proliferation by indoleamine 2,3-dioxygenase-expressing dendritic cells: mediation of suppression by tryptophan metabolites. *J Exp Med* 196:447.

The involvement of IDO in tumor evasion has been implicated in murine models. For example, P815 murine mastocytoma cells transfected with IDO were able to form large and stable tumors when introduced into pre-immunized hosts which would normally reject the tumors outright (Uyttenhove, C., L. Pilotte, I. Theate, V. Stroobant, D. Colau, N. Parmentier, T. Boon, and B. J. Van den Eynde. 2003. Evidence for a tumoral immune resistance mechanism based on tryptophan degradation by indoleamine 2,3-dioxygenase. *Nat Med* 9:1269). The immunosuppressive effect of IDO was completely reversed by the introduction of 1-MT (a chemical with potential toxic effects) leading to renewed tumor rejection.

Due to its ability to suppress immune responses towards endogenous tumor antigens, IDO as well as other immunosuppressive molecules represent ideal targets for immunomodulatory drugs which are used to leverage the efficacy of standard chemotherapeutic agents. In the case of IDO, currently used immunomodulatory drugs pose potential toxic threats towards humans especially if required in large doses.

RNA interference (RNAi) refers to a process of sequence-specific post-transcriptional gene silencing in animals mediated by short interfering RNAs (siRNAs). There exist several different methods for inhibiting gene expression using RNAi such as described for example in WO 02/055692, WO 02/055693, EP 1144623 B1 and WO 03/074654. WO 02/08644 and WO 04/048938 suggest that siRNA technology may be used for inhibiting cancer, however, no studies were demonstrated to support such a contention.

The ability to inhibit IDO as well as inhibit other immunosuppressive tumor derived molecules without the use of detrimental chemicals is desirous. The Applicant has therefore provided a method utilizing siRNA by which tumor derived immunosuppression can be inhibited in a manner that obviates one of more deficiencies of current therapies that may debilitate the immune system and potentially pose damaging and toxic effects upon the body.

SUMMARY OF THE INVENTION

The present invention is a method for the treatment of cancer using short interfering RNA (siRNA). More specifically, the present invention is directed to methods of cancer treatment through the inhibition of tumor derived immunosuppression using siRNA. The invention also encompasses compositions of siRNA useful for the treatment of cancer involving tumor derived immunosuppression.

The invention has been demonstrated to effectively silence desired targeted immunosuppressive molecule(s) (ie. genes encoding such molecule(s)) leading to a decrease in tumor-derived T cell inhibition, an increase in T cell directed tumor lysis, inhibition of tumor growth, delayed tumor formation and a decrease in tumor size.

In embodiments of the present invention, siRNA is used to inhibit one or more immunosuppressive genes such as but not limited to IDO, FasL, VEGF, IL-10, TRAIL, DAF and HLA-G whereby such gene expression leads to immunosuppression and involvement in the formation of a tumor (i.e. development of a cancer). In further embodiments of the present invention, IDO-siRNA is used to treat cancer in subjects where IDO expression leads to tumor evasion and immunosuppression. In still further aspects, the IDO-siRNA is provided as a composition alone or within a liposome. In yet still further aspects, the liposome containing IDO-siRNA is provided within immunoliposomes that target a cancer.

According to an aspect of the present invention is a method for the treatment of cancer involving tumor derived immunosuppression in a subject, the method comprising administering to said subject one or more siRNA constructs capable of inhibiting the expression of an immunosuppressive molecule.

According to another aspect of the present invention is a method for the treatment of cancer involving tumor derived immunosuppression in a subject, the method comprising administering to said subject one or more siRNA constructs directed to an immunosuppressive molecule selected from the group consisting of IDO-siRNA, FasL-siRNA, VEGF-siRNA, IL-10-siRNA, TRAIL-siRNA, DAF-siRNA, HLA-G-siRNA and combinations thereof said siRNA construct capable of substantially inhibiting and/or reducing the expression of said immunosuppressive molecule.

According to yet another aspect of the present invention is a method for the treatment of cancer involving tumor derived immunosuppression in a subject, the method comprising administering to said subject a IDO-siRNA construct, said IDO-siRNA construct capable of inhibiting the expression of said immunosuppressive molecule.

According to another aspect of the present invention is a method for the treatment of cancer involving tumor derived immunosuppression in a subject, the method comprising administering to said subject one or more siRNA constructs capable of inhibiting the expression of an immunosuppressive molecule; and a DC vaccine comprising one or more tumor antigens. The vaccine may further comprise one or more adjuvants. In aspects, the siRNA construct is selected from the group consisting of IDO-siRNA, FasL-siRNA, VEGF-siRNA, IL-10-siRNA, TRAIL-siRNA, DAF-siRNA, HLA-G-siRNA and combinations thereof.

According to still another aspect of the present invention is a method for increasing the efficacy of cancer therapy in a subject, the method comprising:

administering to a subject in need of an effective amount of an siRNA construct directed to an immunosuppressive molecule, wherein said subject is also being administered a cancer therapy selected from the group consisting of small-molecule drugs, angiogenesis inhibitors, tumor vaccine, chemotherapy, immunotherapy, radiation therapy, gene therapy and combinations thereof.

In aspects, the siRNA construct may be selected from the group consisting of IDO-siRNA, FasL-siRNA, VEGF-siRNA, IL-10-siRNA, TRAIL-siRNA, DAF-siRNA, HLA-G-siRNA and combinations thereof, the siRNA construct capable of substantially inhibiting/decreasing the expression of said immunosuppressive molecule.

According to an aspect of the present invention is a medicament comprising a siRNA molecule of the invention. In aspects, this is an immunosuppressive molecule-siRNA. In further aspects, the medicament comprises a DC vaccine which comprises one or more tumor antigens.

According to another aspect of the present invention is an active ingredient comprising a siRNA molecule of the invention. In aspects, the active ingredient is an immunosuppressive molecule-siRNA. In further aspects, the active ingredient may comprise a DC vaccine which comprises one or more tumor antigens.

According to another aspect of the present invention is provided is a composition comprising one or more siRNA constructs directed to an immunosuppressive molecule, and a pharmaceutically acceptable carrier.

According to another aspect of the present invention there is provided a composition comprising one or more siRNA constructs directed to an immunosuppressive molecule, a DC vaccine comprising one or more tumor antigens and a pharmaceutically acceptable carrier.

In aspects of the invention, the siRNA constructs are provided within a suitable vector or carrier. In further aspects of the invention, the siRNA constructs are immunosuppressive molecule-siRNA constructs.

In any aspects of the composition, the siRNA can be administered alone or within liposomes. The liposomes may further be immunoliposomes that are conjugated with an antibody to target the cancer.

According to a further aspect of the present invention, there is provided a method for the treatment of cancer in a mammalian subject, said method comprising administering a therapeutically effective amount of a composition to said subject, said composition comprising an siRNA construct targeted to inhibit the expression of an immunosuppression molecule involved in tumor evasion. In aspects, such immunosuppression molecule may be selected from the group consisting of IDO-siRNA, FasL-siRNA, VEGF-siRNA, IL-10-siRNA, TRAIL-siRNA, DAF-siRNA, HLA-G-siRNA and combinations thereof. In aspects of the invention, the method may further comprise co-administration of a DC vaccine with the composition, the DC vaccine comprising one or more tumor antigens.

According to another aspect of the present invention is the use of an siRNA-IDO construct to silence a targeted endogenous IDO in a mammalian subject, said siRNA-IDO construct reducing expression of said IDO, wherein said reduction in IDO expression results in a decrease in IDO-directed tumoral immunosuppression.

According to a further aspect of the present invention, provided is a method of increasing T-cell proliferation in a mammalian subject, wherein a therapeutically effective amount of an siRNA-IDO construct is administered to said subject, said construct targeting an endogenous IDO, reducing expression of said IDO thereby reducing IDO-directed immunosuppression and T-cell apoptosis.

According to another aspect of the present invention, provided is a method for reversing IDO-directed tumoral immunosuppression in vivo, said method comprising administering intra-tumorally a therapeutically effective amount of an IDO-siRNA construct directed to a targeted endogenous IDO.

According to a further aspect of the present invention are antibody conjugated liposomes comprising one or more siRNA targeted to one or more immunosuppressive genes.

According to a further aspect of the present invention is a composition comprising liposomes comprising one or more siRNA targeted to one or more immunosuppressive genes.

According to a further aspect of the present invention is a method to treat cancer in a subject, the method comprising:
    administering to said subject one or more siRNA targeted to one or more immunosuppressive genes and also administering one or more siRNA targeted to one or more growth factors.

In aspects, this method can further comprise the additional use of a conventional cancer treatment as described herein.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Preferred embodiments of the present invention will now be described more fully with reference to the accompanying drawings:

FIG. 1A shows the silencing efficiency at the transcriptional level as detected by RT-PCR. GAPDH (negative control) and IDO mRNA were detected by RT-PCR 24 h after transfection to assess the efficacy of silencing IDO transcripts. FIG. 1B shows the silencing efficiency at the protein level as detected by Western Blotting. Cells were harvested 48 h after transfection and 100 µg of total protein was extracted for Western Blotting. The blot was labeled with anti-IDO antibody (upper), then stripped off and labeled with anti-β-actin antibody to show that each lane contains equal amount of protein (lower). FIG. 1C shows that silencing IDO preserves tryptophan in B16 culture medium. B16 culture media was measured for tryptophan concentration using HPLC to assess the efficiency of silencing on enzyme functionality. FIG. 1D shows that silencing IDO reduces tryptophan catabolism into kynurenine. B16 culture medium was also measured for kynurenine concentration as detected by HPLC.

FIG. 2A shows that silencing IDO delays tumor onset. $2 \times 10^5$ B16 cells were injected subcutaneously into the hind flanks of B/6 mice. B16 cells were either transfected in vitro with IDO-siRNA or nonsense siRNA prior to injection. Alternatively, wild-type B16 cells suspended in 0.2 ml PBS were injected as an additional negative control. Mice were physically examined every other day for tumor formation. Tumor onset (day 0) was established as the point in time when tumors reached 5 mm in diameter. FIG. 2B shows that silencing IDO slows tumor growth. B/6 mice were injected subcutaneously with $2 \times 10^5$ B16 cells into their hind flanks as described above with respect to FIG. 2A, using a similar subset of B16 cells with the addition of B16 cells pre-treated with 1-MT. Tumor size was measured daily by physical examination.

FIG. 3A shows that silencing IDO reduces CD8+ T cell apoptosis in tumor-bearing mice. $2 \times 10^5$ B16 cells suspended in 0.2 ml PBS were injected subcutaneously into the hind flank of B/6 mice. Mice were physically examined every other day for tumor size. When tumor size reached 5 mm in diameter, mice were divided into two groups; one group was administrated 50 µg IDO-siRNA in 0.2 ml PBS intra-tumorally twice a week, the second group was injected with 0.2 ml PBS to serve as a negative control. When tumor size reached 2000 mm$^3$, mice were sacrificed and CD8$^+$ T cells were isolated from the spleen and lymph nodes using CD8+ MACbeads and stained with FITC-conjugated Annexin-V for subsequent FACS analysis. FIG. 3B shows that silencing IDO reduces the apoptosis of spleenic-derived CD8+ T cells in vitro. $1 \times 10^6$ BALB/c spleen cells were cultured with $1 \times 10^5$ B16 cells. B16 cells were either wild-type (negative control) or had previously been transfected with IDO-siRNA for 24 h in vitro. 18 h after co-culture, spleen cells were collected and double stained with PE-labeled anti-CD8$^+$ antibody and with FITC-conjugated Annexin-V and subsequently submitted for FACS analysis. FIG. 3C shows that silencing IDO reduces the apoptosis of spleenic-derived CD4+ T cells in vitro. Spleen cells were co-cultured with B16 cells as described in B. 18 h after co-culture, spleen cells were collected and double stained with PE-labeled anti-CD4$^+$ antibody and FITC-conjugated Annexin-V and subsequently submitted for FACS analysis. FIG. 3D shows that silencing IDO increases the proportion of CD8+ T cells in tumor-bearing B/6 mice. $2 \times 10^5$ B16 cells were suspended in 0.2 ml PBS and were injected subcutaneously into the hind flank of B/6 mice. Mice were physically examined every other day for tumor size. When tumor size reached 5 mm in diameter, mice were divided into two groups; one group was administrated 50 µg IDO-siRNA in 0.2 ml PBS intra-tumorally twice a week, the second group was injected with 0.2 ml PBS to serve as a negative control. When tumor size reached 2000 mm$^3$, the mice were sacrificed and CD8$^+$ cells from spleen and lymph nodes were isolated with CD8$^+$ MACbeads. CD8$^+$ cells were subsequently stained with FITC-labeled anti-CD8 antibody and analyzed by FACS analysis.

FIG. 4A shows mean tumor volumes in B/6 mice challenged with subcutaneous injection of $2 \times 10^5$ cells of B16 cells. IDO-siRNA bound to liposomes was injected intra-tumorally when tumors reached a size of about 5-7 mm. A control was established by treating cells with transfection reagent alone (mock-silencing). FIG. 4B shows mean tumor volumes in Balb/C mice challenged with subcutaneous injection of $2\times10^5$ B16 cells. IDO-siRNA and control siRNA was delivered as described above with respect to FIG. 4A. FIG. 4C shows mean time for tumor onset in syngeneic C57/BL6 mice challenged with subcutaneous injection of $2\times10^5$ B16 cells. FIG. 4D shows mean weight of tumor (g) at endpoint of observation (death or time elapse) in Balb/C mice challenged with subcutaneous injection of $2\times10^5$ B16 cells.

FIG. 5A shows that silencing IDO reduces tumor-induced suppression of T cell proliferation. $3\times10^5$ IDO-siRNA-transfected or wild-type B16 cells were cultured in complete medium for 48 h. The media was subsequently tested for tryptophan and kynurenine content, and then used for the culture of $2\times10^5$ (per well) B/6 spleenic-derived T cells in a 96-well plate in varying ratios to complete RPMI-1640 medium (20:180 ml, 50:150 ml, 180:20 ml conditioned medium to complete RPMI-1640 medium). Wells were supplemented with 5 μg/pl conA. T cell proliferation was measured by a [$^3$H] thymidine incorporation assay. FIG. 5B shows that IDO-silenced DCs enhance DC-induced T cell proliferation. $5\times10^5$ BALB/c spleenic-derived T cells were co-cultured with $4\times10^5$ IDO-silenced C57/BL6 DCs, mock-silenced or non-silenced DC for 72 h. Cultures containing non-silenced DCs were further separated into 3 group, one group containing 200 μmol/L 1-MT in the medium, one containing 200μ/ml IFN-γ, the other containing only complete medium. T cells were pulsed with 1 μCl [$^3$H]-thymidine for the final 18 h of culture. T cell response was assessed by thymidine incorporation. FIG. 5C shows that IDO-siRNA treatment improves CTL-induced tumor lysis. Naive spleenic-derived T cells from B/6 mice were primed with DCs previously pulsed with tumor lysate to generate B16-specific cytotoxic lymphocytes. CTLs were incubated with IDO-siRNA-treated or wild-type B16 cells (target cells) at different effector:target cell ratios for 4 h. Target cell lysis was determined by LDH release as detected by the Cytotox96 non-radioactive cytotoxicity assay (Promega Corp.). FIG. 5D shows that IDO-siRNA treatment enhances antigen-specific T cell proliferation. 7 days post extraction bone marrow-derived DC transfected with IDO-siRNA, or treated with reagent alone were pulsed with 10 μg/ml of keyhole limpet hemocyanin (KLH) for 24 h. DCs were then activated with LPS+TNFα for 24 h. Antigen-pulsed DCs ($2\times10^6$ cells/mouse) were injected subcutaneously into syngeneic mice. Mice were sacrificed after 10 days and cell suspensions were prepared from the draining lymph nodes. These cells were cultured in 96-well plates at a concentration of $4\times10^5$ cells/well in the presence or absence of antigen for 72 h. The cells were pulsed with 1 μCl [$^3$H]-thymidine for the last 18 h for subsequent thymidine incorporation assay.

DETAILED DESCRIPTION OF THE PREFERRED EMBODIMENTS

Figure 1:
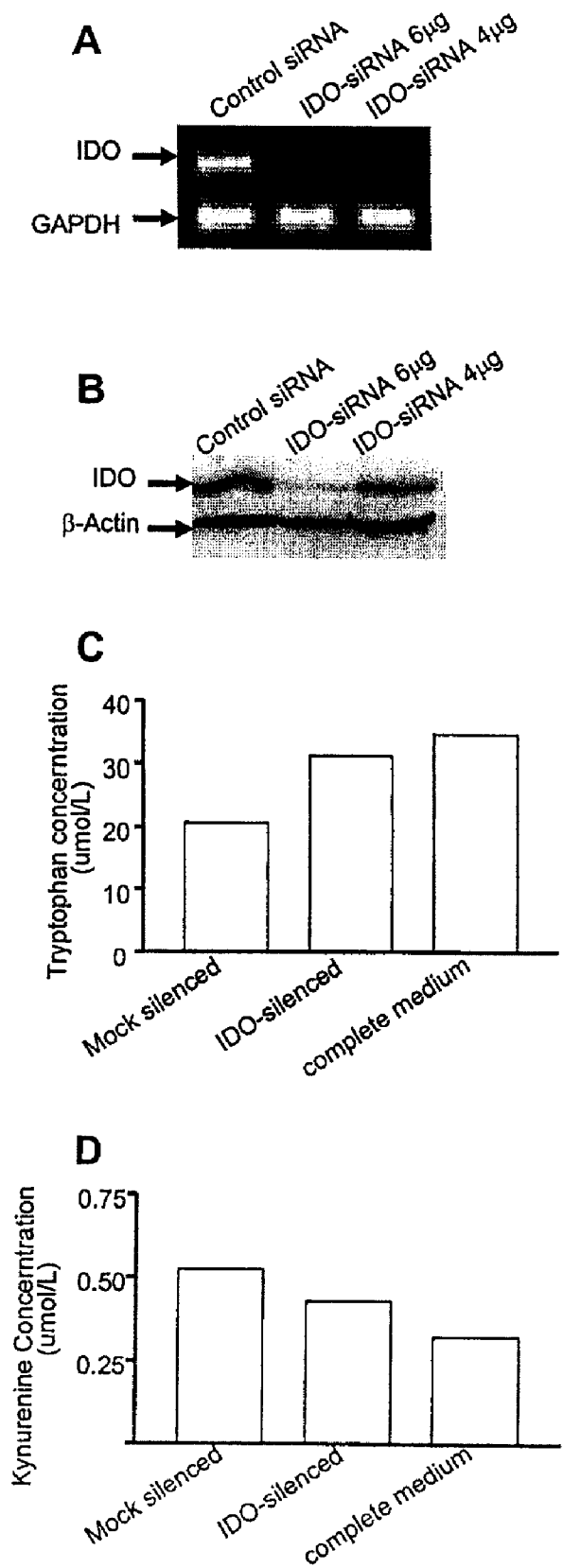
FIGS. 1A through 1D demonstrate that IDO is efficiently silenced by siRNA. $5 \times 10^5$ B16 cells were seeded into plates and transfected with 4-6 µg of IDO-siRNA or nonsense siRNA (negative control) using lipofectamine 2000 reagent.

The present invention is a method for the treatment of cancer using short interfering RNA (siRNA). The Applicant has effectively demonstrated for the first time that siRNA can be used for the inhibition of tumor derived immunosuppression and as such provides a novel method for cancer treatment. Thus RNA interference may now be used as a cancer therapeutic functioning through the reinstallation of anti-cancer immunity.

An siRNA-based therapeutic approach is a more targeted and potentially safer approach to the treatment of cancer in comparison to known chemical methods. Furthermore, the method of the present invention is using targeted siRNA is demonstrated to be effective to treat cancer whether providing substantially complete silencing of immunosuppressive genes or partial silencing of immunosuppressive genes. SiRNA partial silencing still leads to the suppression of the defense system of the tumor allowing for reinstallation of anti-tumor immunity. This is ubiquitously applicable in the treatment of a variety of cancers in comparison to known chemical cancer treatments.

In the method of the invention, siRNA is specifically targeted to an immuno suppressive molecule to decrease or substantially inhibit its expression. Such immunosuppressive molecules may include but not be limited to IDO, FasL, VEGF, IL-10, TRAIL, DAF(CD55), HLA-G and any combinations thereof. Indoleamine 2,3-dioxygenase (IDO) is a tryptophan catabolizing enzyme. IDO is the rate-limiting enzyme in the kynurenine pathway which converts the essential amino acid L-tryptophan to L-kynurenine. FasL is a type II membrane protein belonging to the TNF family of cytokines. FasL induces apoptosis when it binds to cells expressing the Fas antigen. FasL was first discovered on the cell surface of T cells and NK cells. Expressed on the cell surface of activated T cells, FasL kills T cells and activated B cells leading to down-regulation of the immune response. The full length of FasL contains 281 amino acid residues, consisting of the transmembrane domain, extracellular domain and the cytoplasmic region. VEGF (also known as VEGF-A) is a member of a family of structurally related proteins that act as ligands (molecules that bind to receptors) for the family of VEGF receptors. VEGF exerts its effects on the development of new blood vessels (angiogenesis) and survival of immature blood vessels (vascular maintenance) by binding to and activating two structurally related membrane receptor tyrosine kinases, VEGF receptor-1 and VEGF receptor-2, which are expressed by endothelial cells in the blood vessel wall. When VEGF binds to these receptors a signal cascade that ultimately stimulates vascular endothelial cell growth, survival and proliferation is initiated. Endothelial cells have roles in processes as varied as vasoconstriction/vasodilation and antigen presentation, and are essential components of all blood vessels, whether capillaries, veins or arteries. Thus, through stimulating endothelial cells, VEGF plays a central role in angiogenesis. Tumor necrosis factor (TNF)-related apoptosis-inducing ligand (TRAIL) is a proapoptotic member of the TNF family of type II membrane proteins, which constitutes one component of T cell cytotoxicity. IL-10 is an antiinflammatory and immunosuppressive substance produced within the body. IL-10 plays a role in the regulation of immune responses. It is secreted by antigen-presenting cells, promotes the development of immunologic tolerance, and suppresses the production of inflammatory cytokines. CD55 is known also as decay-accelerating factor (abbr. DAF). It is identical with the Cromer blood group antigen (Wang et al, 1998). Primarily, CD55 is a complement regulatory protein that interrupts the complement cascade by preventing the assembly and/or promoting the dissociation of C3 and C5 convertases and thus prevents complement mediated cell injury and helps to maintain vascular function in inflammation. The class I gene HLA-G has been detected on the surface of some human oocytes, preimplantation embryos and placental cells. In addition, HLA-G: binds peptides leading to antiviral function; contributes to immunosurveillance by interacting with T cell receptor inducing T cell tolerance and apoptosis of activated cytotoxic T cells; and, modulates secretion of cytokines (IL1, IL3, IL10 and TNFα0 ) by binding to NK cell receptors.

The invention also encompasses the use of one or more siRNA of immunosuppressing genes and one or more growth factors such as but not limited to VEGF, FGF and hCG. Such growth factors act as angiogenesis switches as well as providing proliferative signals for trophoblast and endothelial cells. Growth factors are needed for the growth and survival of various cancers and are essential for cancer progression. Therefore the anticancer methods of the invention using siRNA to inhibit an immunosuppressive molecule can be combined with siRNA targeted to one or more growth factors. Such combination therapy contributes to a synergistic effect to treat cancer.

The invention also encompasses the use of one or more siRNA of immunosuppressing genes with siRNA directed to an oncogene as this may also act to increase the efficacy of the cancer treatment. Suitable oncogenes include but are not limited to Ras, Myc, Fos, Jun and Erg-2.

As such, the siRNA methods of the invention using siRNA targeted to an immunosuppressive gene(s), may be used in combination with siRNA targeted to one or more growth factors and/or oncogenes as is understood by one skill in the art.

RNA interference (RNAi) is a mechanism to suppress gene expression in a sequence specific manner. RNA Interference (RNAi) is highly effective and used methodology for suppression of specific gene function in eukaryotic cells. When applied to invertebrate cells and organisms, RNAi entails the degradation of target mRNA upon transfection of short interfering RNA (siRNA) oligos or short-hairpin RNA (shRNA) encoding vectors. Various methods of RNAi have been described and are generally known for the altering gene expression in plant cells, drosophila and human melanoma cells as is described for example in U.S. Patent Application No. 2002/0162126A1, PCT/US03/05028, PCT/US01/10188, PCT/EP01/13968 and U.S. Patent Application No. 2002/0173478A1 (the disclosures of which are hereby incorporated by reference in their entirety). The siRNA for use in the methods and compositions of the invention are selected to target a desired immunosuppressive molecule or combinations of such molecules. In this manner they are targeted to various RNAs corresponding to a target gene, and in the present invention targeted to an immunosuppressive molecule. It is understood by one of skill in the art that the siRNA as herein described may also include altered siRNA that is a hybrid DNA/RNA construct or any equivalent thereof, double-stranded RNA, microRNA (miRNA), as well as siRNA forms such as siRNA duplications, small hairpin RNA (shRNA) in viral and non-viral vectors and siRNA or shRNA in carriers.

In aspects of the invention, the siRNA of the invention (referred to herein as immunosuppressive molecule-siRNA when made directed to a specific molecule) can be made by several different methods such as by chemical synthesis, expressed from a vector by in vitro transcription, siRNA expression vectors, PCR expression cassettes or enzymatically synthesized as is understood by one of skill in the art. In aspects, the siRNA molecules of the invention may be independently about 18 to about 24 nucleotides in length and any length thereinbetween. It may also be possible to use siRNA molecules slightly greater in length that about 24 nucleotides or slightly shorter in length than about 18 nucleotides as is understood by one of skill in the art.

The methods and compositions of the invention are useful in the treatment of any tumors (i.e. cancer) where there is tumor derived immunosuppression leading to tumor evasion. The methods and compositions of the invention are used to silence the immunosuppressive molecule (ie. the gene encoding that molecule) that is being targeted leading to a decrease in the molecules function, a decrease in T cell-derived T cell inhibition (both in proliferation and apoptosis) and an increase in T cell-directed tumor lysis. Silencing of the immunosuppressive molecule(s) functions to inhibit tumor growth and delay tumor formation in vivo as well as postpone tumor onset time and decrease tumor size. As such, cancers that may be treated by the methods and compositions of the invention may include any type of tumor where there is tumor derived immunosuppression such as but not limited to melanoma, leukemias, lymphoma, cancers in the oral cavity, esophagus, stomach, colon and rectum, liver, pancreas, larynx, lung, breast, cervix, uterus, ovary, prostate, testis, bladder, kidney, thyroid, brain and bone.

The present invention provides methods of using therapeutic compositions comprising siRNA designed to target a specific mRNA of an immunosuppressive molecule such as for example IDO. In embodiments of the invention, the therapeutic compositions of the invention may also include activated and non-activated altered (i.e. transformed) immune cells that contain the siRNA such as for example tumor-antigen pulsed dendritic cells (DC). A feature of DC is their capacity to migrate or home to T-dependent regions of lymphoid tissues where DC may affect T cell activity and elicit a modulated immune response. In this manner compositions comprising DC containing siRNA specifically designed to degrade mRNA encoding an immunosuppressive gene such that the transformed DC leads to a lack of expression of the gene and as a result affect the activity of T cells to modulate an immune response. Such DC may be provided as vaccine compositions for administration to a mammalian subject or as compositions for ex vivo approaches for the treatment of cells, tissues and/or organs for transplantation as described in Example 7 provided herein. The DC are thus provided as a tumor vaccine that can be used in combination with the immunosuppressive molecule-siRNA of the invention. Methods for silencing genes in dendritic cells is taught in the Applicant's PCT CA03/00867 (the disclosure of which is herein incorporated in its entirety).

Compositions of the invention whether immunosuppressive agent-siRNA or additionally comprising a DC having an immunosuppressive gene silenced therein may contain pharmaceutically acceptable carriers or excipients suitable for rendering the mixture administrable orally or parenteraly, intravenously, intradermally, intramuscularly or subcutaneously or transdermally. The transformed immune cells and/or siRNA may be admixed or compounded with any conventional, pharmaceutically acceptable carrier or excipient as is known to those of skill in the art.

As used herein, the term "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. Except insofar as any conventional media or agent is incompatible with the compositions of this invention, its use in the therapeutic formulation is contemplated. Supplementary active ingredients can also be incorporated into the pharmaceutical formulations.

It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

It is also understood by one of skill in the art that the compositions of the invention may be for in vitro, ex vivo or in vivo use.

The therapeutically effective amount of active agent to be included in the pharmaceutical composition of the invention depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and in aspects from about 0.1 to about 100 mg/kg.

While it is possible for the agents to be administered as the raw substances, it is desirable, in view of their potency, to present them as a pharmaceutical formulation. The formulations of the present invention for mammalian subject use comprise the agent, together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier, which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents, which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, metacresol, phenol and benzalkonium chloride. Such materials are of special value when the formulations are presented in multidose containers.

Compositions of the invention comprising a selected targeting siRNA can also comprise one or more suitable adjuvants. In this embodiment siRNA can be used as a vaccine in order to stimulate or inhibit T cell activity and polarize cytokine production by these T cells. As is well known to those of ordinary skill in the art, the ability of an immunogen to induce/elicit an immune response can be improved if, regardless of administration formulation (i.e. recombinant virus, nucleic acid, peptide), the immunogen is co-administered with an adjuvant. Adjuvants are described and discussed in "Vaccine Design-the Subunit and Adjuvant Approach" (edited by Powell and Newman, 'Plenum Press, New York, U.S.A., pp. 61-79 and 141-228 (1995). Adjuvants typically enhance the immunogenicity of an immunogen but are not necessarily immunogenic in and of themselves. Adjuvants may act by retaining the immunogen locally near the site of administration to produce a depot effect facilitating a slow, sustained release of immunizing agent to cells of the immune system. Adjuvants can also attract cells of the, immune system to an immunogen depot and stimulate such cells to elicit immune responses. As such, embodiments of this invention encompass compositions further comprising adjuvants.

Desirable characteristics of ideal adjuvants include:
1) lack of toxicity:
2) ability to stimulate a long-lasting immune response;
3) simplicity of manufacture and stability in long-term storage;
4) ability to elicit both cellular and humoral responses to antigens administered by various routes, if required:
5) synergy with other adjuvants;
6) capability of selectively interacting with populations of antigen presenting cells (APC);
7) ability to specifically elicit appropriate Tr, TR1 or TH2 cell-specific immune responses; and
8) ability to selectively increase appropriate antibody isotype levels (for example, IgA) against antigens/immunogens.

Suitable adjuvants include, amongst others, aluminium hydroxide, aluminium phosphate, amphigen, tocophenols, monophosphenyl lipid A, muramyl dipeptide and saponins such as Quill A. Preferably, the adjuvants to be used in the tolerance therapy according to the invention are mucosal adjuvants such as the cholera toxine B-subunit or carbomers, which bind to the mucosal epithelium. The amount of adjuvant depending on the nature of the adjuvant itself as is understood by one of skill in the art.

The siRNA of the present invention may be provided systemically as described herein above or more targeted to be tumor-specific so that the siRNA is delivered to the cancer. As understood by one of skill in the art, the siRNA of the invention may be used within conventional liposomes, specialized liposomes, lipid formulations and immunoliposomes.

The liposomes may be unilamellar or multilamellar and are formed of constituents selected from phosphatidylcholine, dipalmitoylphosphatidylcholine, cholesterol, phosphatidylethanolamine, phosphatidylserine, demyristoylphosphatidylcholine and combinations thereof. The multilamellar liposomes comprise multilamellar vesicles of similar composition to unilamellar vesicles, but are prepared so as to result in a plurality of compartments in which the silver component in solution or emulsion is entrapped. Additionally, other adjuvants and modifiers may be included in the liposomal formulation such as polyethyleneglycol, or other materials.

While a suitable formulation of liposome includes dipalmitoyl-phosphatidylcholine:cholesterol (1:1) it is understood by those skilled in the art that any number of liposome bilayer compositions can be used in the composition of the present invention. Liposomes may be prepared by a variety of known methods such as those disclosed in U.S. Pat. No. 4,235,871 and in RRC, Liposomes: A Practical Approach. IRL Press, Oxford, 1990, pages 33-101.

The liposomes containing the siRNA may have modifications such as having non-polymer molecules bound to the exterior of the liposome such as haptens, enzymes, antibodies or antibody fragments, cytokines and hormones and other small proteins, polypeptides or non-protein molecules which confer a desired enzymatic or surface recognition feature to the liposome. Surface molecules which preferentially target the liposome to specific organs or cell types include for example antibodies which target the liposomes to cells bearing specific antigens. Techniques for coupling such molecules are well known to those skilled in the art (see for example U.S. Pat. No. 4,762,915 the disclosure of which is incorporated herein by reference). Alternatively, or in conjunction, one skilled in the art would understand that any number of lipids bearing a positive or negative net charge may be used to alter the surface charge or surface charge density of the liposome membrane.

The liposomes can also incorporate thermal sensitive or pH sensitive lipids as a component of the lipid bilayer to provide controlled degradation of the lipid vesicle membrane.

Liposome formulations for use with the siRNA of the present invention may also be as that disclosed in WO 2005/105152 (the disclosure of which is incorporated herein in its entirety). Briefly, such formulations comprise phospholipids and steroids as the lipid component. These formulations help to target the molecules associated therewith to in vivo locations without the use of an antibody or other molecule.

Figure 9:
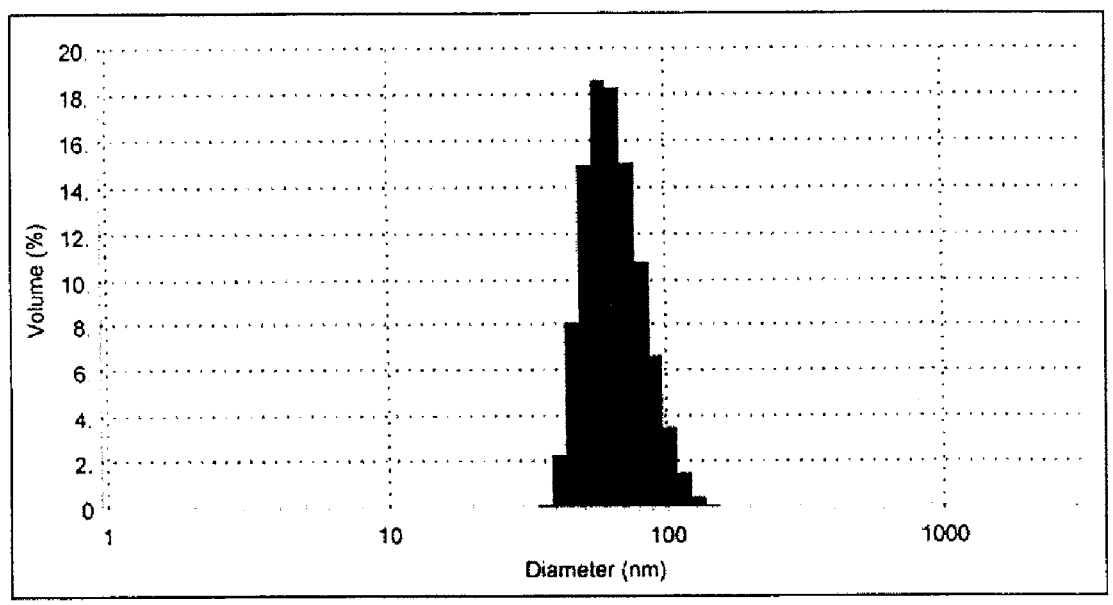
FIG. 9 is a size distribution of VEGFR-specific siRNA-loaded immunoliposomes prepared by rapid extrusion. The mean diameter of the immunoliposomes encapsulating the siRNA is 73 nm.
Figure 10:
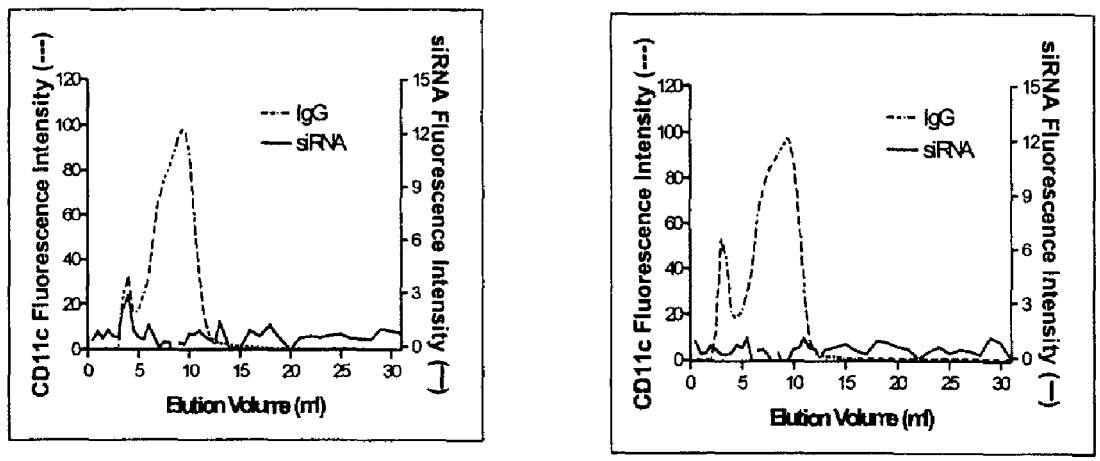
FIG. 10 is a gel filtration elution profile of VEGFR-specific, siRNA-loaded immunoliposomes. VGFR-specific (Ycom 1D3) mAbs and siRNA were fluorescently labeled with R-PE and Alexa 488, respectively. Passing immunoliposome dispersions through a Sepharose CL-4B gel filtration column allowed for separation of the immunoliposomes from unconjugated mAb and from exteriorized RNase III digested siRNA. In the first panel, the comigration of the interiorized siRNA and the mAb demonstrated the siRNA and the targeting mAb were incorporated in the same structure. The second panel shows the elution profile of control immunoliposomes which do not contain encapsulated siRNA.
Figure 11:
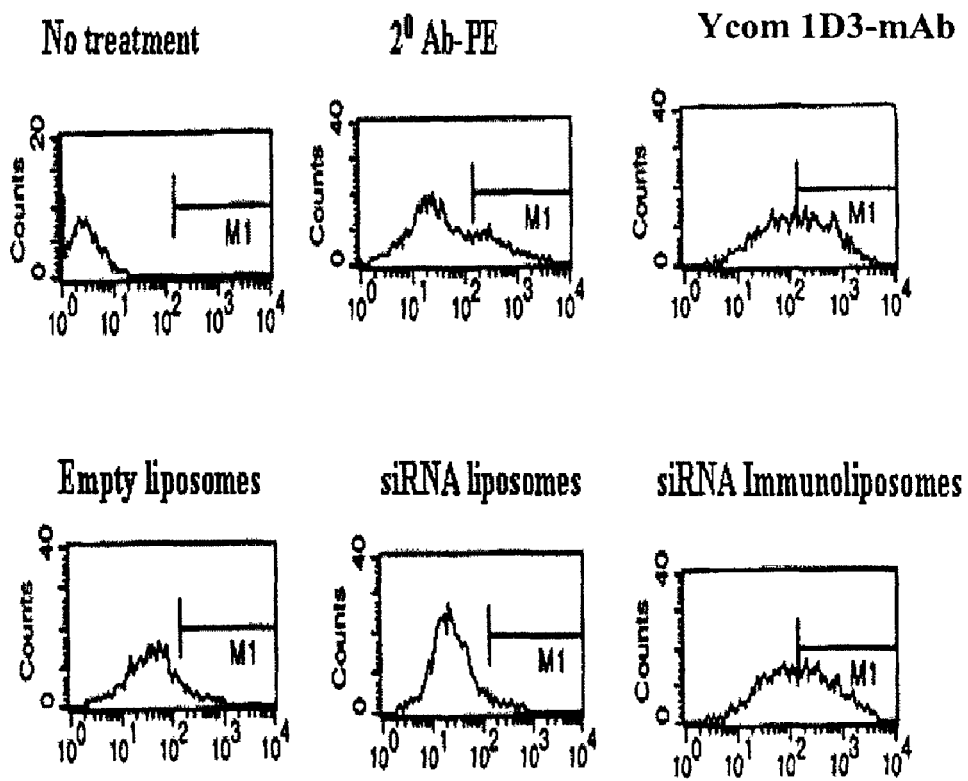
FIG. 11 is a FACS analysis of VEGFR-immunoliposomes binding to B16 cells. B16 cells were incubated for 30 minutes at 40° C. with: liposomes containing neither siRNA nor Ycom 1D3 mAb (empty liposomes), liposomes containing siRNA, but not conjugated to Ycom 1D3 mAb (siRNA liposomes), or Ycom 1D3 mAb-conjugated liposomes which contain siRNA (siRNA immunoliposome). Subsequently, a secondary anti-IgG mAb labeled with PE was added to detect whether immunoliposomes had bound to B16 cells. Controls included: no treatment as a negative control, treatment with the secondary antibody only (20 Ab-PE), and treatment with Ycom 1D3 mAb followed by incubation with the PE-labeled secondary anti-IgG mAb.

In one such aspect of the invention antibody-conjugated liposomes, termed immunoliposomes, carry siRNA within their aqueous compartment of the structure (siRNA-immunoliposome). siRNA-immunoliposomes can specifically deliver siRNA to the cells possessing a unique antigenic marker recognized by the antibody portion of the immunoliposome. Thus, immunoliposomes are ideal for the in vivo delivery of siRNA to target tissues due to simplicity of manufacture and proven cell-specific specificity. siRNA-immunoliposomes to carry siRNA and target B16 cells have been made and described herein (FIGS. 9, 10).

In order to generate a mass-producible vaccination strategy, many investigators have sought tumor-specific antigens. Tumor-specific antigens may be used herein in conjunction with the liposomes containing the desired siRNA. MAGE genes, including MAGE1, have been identified and are suitable as tumor-specific antigens for use in the present invention. The entire coding sequences for all MAGE genes are located within the last exon, which exhibits 64 to 85% homology with the sequence of MAGE1. In the present invention siRNA is loaded into liposomes following conjugation with an antibody against MAGE. As an alternative strategy, siRNA-liposomes are conjugated with an antibody against VEGF receptor that is highly expressed in various tumor cells including melanoma. The administration of IDO-siRNA-immunoliposome (IDO-IL-siRNA) conjugated with MAGE or VEGF receptor antibodies will specifically silence genes in DC while not causing substantial systemic gene silencing.

As such, compositions of siRNA of the present invention may be provided within antibody labelled liposomes (immunoliposomes) or antibody-double stranded RNA complexes. In this aspect, the immunosuppressive molecule-siRNA is specifically targeted to a particular cell or tissue type to elicit a localized effect on T cell activity. Specifically, the liposomes are modified to have antibodies on their surface that target a specific cell or tissue type. Methods for making of such immuno-liposomal compositions are known in the art and are described for example in Selvam M. P., et.al., 1996. Antiviral Res. Dec;33(1):11-20 (the disclosure of which is incorporated herein in its entirety).

It is also within the scope of the present invention to combine any of the methods and any of the compositions disclosed herein with conventional cancer therapies and various drugs in order to enhance the efficacy of such therapies through either reducing the doses/toxicity of conventional therapies and/or to increase the sensitivity of conventional therapies. One conventional therapy is the use of radiation therapy. Another conventional therapy is the use of chemotherapeutic drugs that can be divided into: alkylating agents, antimetabolites, anthracyclines, plant alkaloids, topoisomerase inhibitors, and antitumour agents. All of these drugs affect cell division or DNA synthesis and function in some way. Other newer conventional cancer therapies are newer agents that don't directly interfere with DNA. Examples of such newer agents for which to combine with the present invention may include for example "small-molecule" drugs that block specific enzymes and GFRs involved in cancer cell growth. These drugs are also called signal-transduction inhibitors such as Gleevec® (STI-571 or imatinib mesylate) and Iressa® (ZD1839 or gefitinib). Apoptosis-inducing drugs cause cancer cells to undergo apoptosis (cell death) by interfering with proteins involved in the process and an example of such a drug is Velcade® (bortezomib) that causes cancer cells to die by blocking enzymes called proteasomes, which help to regulate cell function and growth. Another apoptosis-inducing drug called Genasense™ (oblimersen), which is presently available in clinical trials, is being studied to treat leukemia, non-Hodgkin's lymphoma, and solid tumors. Genasense blocks the production of a protein known as BCL-2, which promotes the survival of tumor cells. By blocking BCL-2, Genasense leaves the cancer cells more vulnerable to anticancer drugs.

Monoclonal antibodies, cancer vaccines, angiogenesis inhibitors, and gene therapy are targeted therapies that can also be combined with the siRNA method of the invention because they also interfere with the growth of cancer cells.

To summarize, in this aspect, the immunosuppressive molecule-siRNA of the present invention can be combined with a therapy such as but not limited to one or more of a tumor vaccine, chemotherapy, immunotherapy and radiation therapy.

Indolamine 2,3-dioxygenase (IDO)

In one representative embodiment of the present invention, a murine melanoma model was used in which IDO-siRNA was used to silence IDO leading to the suppression of T cell apoptosis and inhibition of tumor growth. Treatment with IDO-siRNA in B16-bearing mice successfully postponed tumor onset and significantly decreased tumor size. Immune recovery was mainly achieved through rescue of T cell proliferation and through the enhancement of tumor-specific lysis. Specifically B16 cells were liposome transfected with IDO-siRNA to efficiently silence IDO. A pQuiet-1U6 plasmid vector (obtained from Welgen Inc., Worcester, Mass.) was used to achieve this transfection, but it can be appreciated that other vector systems could be used. It can further be appreciated that while liposome transfection was carried out with Lipofectamine 2000 reagent, other suitable transfection reagents could be substituted. Upon transfection, silencing of IDO was observed at both the level of transcription, and at the protein level, as detected by RT-PCT and Western blotting respectively.

IDO silencing was also investigated with respect to enzyme function. Being the rate-limiting enzyme of the kynurenine pathway, IDO is responsible for the complete catabolysis of tryptophan into kynurenine. Following liposome transfection, HPLC analysis identified a significant decrease in the functionality of the IDO enzyme, suggesting the silencing method of the present invention was efficient in suppressing IDO at the level of enzyme function.

In addition to the above noted in vitro silencing ability in vivo silencing by challenging mice with pre-treated B16 cells was demonstrated. Although the pretreatment of B16 cells represents a non-realistic ideal as it requires the derivation of tumors from cells which have been treated prior to oncogenesis, the methodology represents an initial step to demonstrate the potential of treatment. Applicants found that pretreatment resulted in substantial delay in tumor onset as well as a significant decrease in tumor size.

In vivo siRNA-derived therapy was also investigated. Both syngeneic and allogeneic mice were subject to intra-tumoral IDO-siRNA treatment which led to substantial reduction in tumor size, as well as delay in tumor onset. As such, the present invention clearly exhibits profound potential for the in vivo treatment of melanoma and possibly other cancers where there is tumor derived immunosuppression.

Again, IDO-derived inhibition is thought to function through two distinct mechanisms, one targeting the proliferation of locally responding T cells, while the other inducing apoptosis of them. Focusing on the latter mechanism, the difference in T cell apoptosis upon IDO-siRNA treatment was characterized and a much smaller proportion of all T cells undergoing apoptosis when T cells were cultured with IDO-siRNA treated B16 cells was identified. The present invention also demonstrates that IDO-derived apoptosis targets CD8+ T cells in preference to CD4+ T cells as indicated by the greater rescue of CD8+ T cells undergoing apoptosis upon IDO-siRNA treatment.

There was in vitro anti-proliferative effect imposed by B16 cells on locally proliferating T cells by culturing pre-activated T cells with supernatant from B16 cells. IDO is a soluble enzyme and hence it functions throughout the local microenvironment and not directly on the surface of the cell. Upon addition of high volumes of B16 supernatent there was significant reduction in T cell proliferation. Applicants observed that this reduction substantially declined when the supernatant added was obtained from B16 cells previously silenced by IDO-siRNA, further supporting that both tumor-derived T cell apoptosis and tumor-driven anti-proliferative effects can be inhibited through IDO-siRNA treatment.

Additional confirmation of the true inhibitory role of IDO arose from an additional [$^3$H] incorporation assay whereby mixed leukocyte reaction (MLR) was performed with spleenic-derived T cells and DCs transfected to express varying amounts of IDO. Both IDO-siRNA-derived treatment and 1-MT treatment of DCs prior to MLR lead to substantial rescue of T-cell proliferation. Such experiments help to prove to the role of T cell inhibition by IDO alone and also suggest that IDO-derived inhibition may manifest through local APCs.

Using a tumor-lysate-based dendritic cell vaccine as previously described (37) the effects of silencing on the rescue of directed immunity was characterized. Sets of B16-specific T cells were generated to characterize CTL-derived lysis of B16 cells. Anti-tumor immunity involves a complex interaction between both tumor cells and CTL with lysis being respectively induced by both sides and targeted against each other. The rescue response of siRNA on the targeted destruction of tumor cells was characterized which is the optimal situation for cancer therapy representing a natural and non-detrimental removal of tumor cells. Applicants observed a dramatic increase in the specific lysis of B16 cells when co-cultured with B16-specific cytotoxic CD8+ T lymphocytes indicating the rescue of directed immunity. Taken in its entirety the mechanistic data suggest profound potential for IDO-siRNA derived therapy on various levels. It was observed that IDO-siRNA treatment reduces tumor-derived T cell apoptosis and tumor-derived inhibition of T cell proliferation. IDO-siRNA treatment also improves DC-derived T cell proliferation and improves tumor lysis.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Materials and Methods

Animal and Cell Lines

Male C57BL/6 and BALB/c mice were purchased from Jackson laboratories (Bar Harbour, Me.). A murine melanoma cell line established from a C57BL/6 mouse designated B16F10 was obtained from American Type Culture Collection (ATCC, Manassas, Va.). B16 cells were cultured in RPMI1640 medium (sigma) with 10% fetal bovine serum, L-glutamine, penicillin and streptomycin at 37° C. in 5% $CO_2$ incubator.

IDO-specific siRNA expression vectors siRNA expression vectors were constructed using the pQuiet plasmid (welgen Inc.). Specific IDO-siRNA inserts were designed according to manufacturer's instruction. The oligonucleotide contained a 19-mer hairpin sequences specific to the IDO mRNA target, a loop sequence separating the two complementary domains, a two nucleotide overhang at the 3' end, a poly thymidine stretch to terminate transcription and a 5' single-stranded overhang for ligation into the pQuiet vector using the BgI I and Xob I cut sites. Both sense and anti-sense hairpin siRNA-encoding oligonucleotides were annealed as an insert. The target site in endogenous IDO is 5'-GTT CTA GAA GGA TCC TTG A (SEQ ID NO: 1). IDO-expressing vectors were amplified in E. coli and were purified using the Qiagen kit (Qiagen ,Inc. Valencia, Calif.).

Gene Silencing

Transfection of siRNA in B16 cells was carried out using Lipofectamine 2000 reagent (Invitrogen, Calif.). Briefly, cells were plated into either 12-well plates ($2 \times 10^5$ cells per well) or six-well plates ($5 \times 10^5$) and allowed to grow overnight in 1 or 2 ml of complete medium without antibiotics. 4 μg or 6 μg of IDO-siRNA-containing plasmid was incubated with 10 μl or μl of Lipofectamine 2000 reagent in 250 μl of Optimal serum-reduced medium at room temperature for 20 min. The mixture was then added to B16 cell cultures exhibiting 90%-95% confluency. Negative controls were established by treating B16 cells with transfection reagent alone (mock control), nonsense siRNA, or alternately cells were non-treated. 4 h after the start of transfection, 200 U/ml of IFN-r was added to the medium. 24-48 h later, transfected B16 cells were washed and used for subsequent experiments.

Transfection of siRNA in DCs was carried out as described previously [6]. Briefly, 4 μg or 6 μg of IDO-siRNA-containing plasmid was incubated with 28 μl or 42 μl of Gensilencer reagent (Gene Therapy Systems, San Diego, Calif.) in 50 μl of RPMbI-1640 (serum free) medium at room temperature for 30 min. The mixture was then added to 400 μl of B16 cell culture in 6-well plate with 60% confluence. Negative controls were established by treated B16 cells with transfection reagent alone (mock control), nonsense siRNA, or alternatively cells were non-treated. After 4 h of incubation an equal volume of RPMI-1640 supplemented with 20% FCS was added to cell suspensions and 200 U/ml of IFN-r was added to the medium. 24-48 h later, transfected DCs were washed and used for subsequent experiments.

RT-PCR

Total RNA from IDO-silenced, nonsense-siRNA-silenced, or mock- transfected B16 cells was isolated using TRIzol reagent (Gibco BRL) as per the manufacturer's instructions. First strand cDNA was synthesized using an RNA PCR kit (Gibco BRL) with the supplied oligo d(T)16 primer. One μmol of reverse transcription reaction product was used for subsequent PCR reaction. The primers used for IDO flanked the IDO-siRNA target sequences (forward primer 5'-GGGCTTTGCTCTACCACATCCACT-3' (SEQ ID NO: 2), reverse primer 5'-ACATCGTCATCCCCTCGGTTCC-3' (SEQ ID NO: 3). GAPDH (internal negative control) primers were used as previously described[7]. PCR conditions used were as follows: 94° C. for 30s, 58° C. for 30s, and 72° C. for 30s, and PCR was conducted for 30 cycles. PCR products were visualized using gel electrophoresis by staining with ethidium bromide in a 1.5% agarose gel.

Western Blot

Cytoplasmic extracts were prepared from IDO-silenced and control B16 cells mechanically released from tissue culture plates by scraping in cold PBS. Cells were collected by centrifugation (800×g), and then resuspended in buffer A [10 mM HEPES (pH 7.9), 10 mM KCl, 0.1 mM EDTA, 0.1 mM EDTA, 0.1% NP40, 1 mM DTT, and 0.5 mM phenylmethylsulfonyl fluoride] with Complete™ protein inhibitor (Roche Diagnostics, Laval, QC). Protein content was determined (Bio-Rad Laboratories, Mississauga, ON) and 100 μg of each cell lysate was resolved on 12% SDS-PAGE, transferred to nitrocellulose membrane (Bio-Rad Laboratories), blocked with 5% fat-free milk (Carnation) and 3% BSA in TBS-T (0.25% Tween-20, probed with the appropriate antibodies according to the manufacturer's instructions, and visualized by an enhanced chemiluminescence assay (Amersham Pharmacia Biotech, Bale DÚrfé, QC).

HPLC

Twenty-five microliters of 15% perchloric acid was added to 50 μL of culture supernatant to precipitate proteins. After incubation at room temperature for 10 min the samples were centrifuged at 11,500 rpm for 3 min. Sample pH was raised to approximately 4 by addition of 20 μL of a citrate buffer (containing 200 μL of 2 M citric acid with 280 μL of 10 M sodium hydroxide and 480 μL of reverse osmosis water). The samples were then mixed and centrifuged at 11,500 rpm for an additional 3 min. Seventy-five microliters of clear supernatant was loaded into a HPLC column (Hewlett-Packard 1090). Analytes were separated using a Spherisorb C8. Tryptophan was detected fluorometrically using excitation and emission wavelengths of 253 nm and 313 nm, respectively whereas kynurenine was detected with the UV-VIS detector set to 360 nm. Peak area and quantitation was determined using Agilent Chemstation software.

Generation of Bone Marrow-Derived Dendritic Cells

Generation of bone marrow-derived DC was performed as previously described [8]. In brief, bone marrow cells were flushed from the femurs and tibias of tolerant, rejective, and naive mice, washed and cultured at $2 \times 10^6$ cells per well in 24-well plates (Corning, N.Y.) in 2 ml RPMI 1640 (GIBCO Life Technologies, Ontario, Canada) media supplemented with 10% fetal-calf serum (FCS, GIBCO), 100 U/ml of penicillin, 100 μg/ml of streptomycin, 50 μM of 2-mercaptoethanol (GIBCO), 10 ng/ml of recombinant murine GM-CSF (Peprotech, Rocky Hill, N.J.) and 10 ng/ml of IL-4 (Peprotech). Non-adherent cells were removed after 48 h of culture, and fresh medium was added every 48 h. DC were used for in vitro experiments after 7 days of culture.

Flow Cytometry

Phenotypic analysis of isolated or cultured DCs was performed on a FACScan (Becton Dickinson, San Jose, Calif.). All antibodies were purchased from BD PharMingen (San Diego, Calif.). T cell subsets were analyzed by staining with PE-conjugated CD4 or CD8 mAbs. Apoptosis of T cells was determined by double staining with above antibodies and FITC-conjugated Annexin-V. All flow cytometric analyses were performed using appropriate isotype controls.

Isolation of CD8$^+$ Cells

CD8$^+$ cells were isolated from spleen cell and lymph nodes using CD8$^+$ Macbeads according to the manufacture's guidance.

CTL-Derived Lysis Assay

Cytotoxic activity was measure with a CytoTox 96 non-radioactive cytotoxicity assay kit (Promega corp, Wis.) under the guidance of the manufacturer's instructions. Briefly, this assay quantitatively detects lactate dehydrogenase (LDH) release. LDH is released upon cell lysis in the same way as $^{51}$Cr is released. Released LDH in culture supernatants was detected after a 30 min incubation using a coupled enzymatic assay. The density of the color formed is proportional to the number of lysed cells. Absorbance data was collected using a 96-well plate reader set at 490 nm. Target cells B16 (5,000) were plated in triplicates in a U-bottom 96-well tissue culture plate and incubated for 4 h with various ratios of effector to target cells. Fifty-microlitre aliquots from all wells were transferred to a fresh 96-well plate after incubation. Fifty microlitres of the substrate mix was added to each well of the plate and incubated at room temperature for 30 min in the dark. Fifty microlitres of a stop solution was then added to each well before absorbance measurements were taken. Maximal release of LDH was recorded by incubating the target cells with lysis solution. Target cells without effector cells were used as a negative control (spontaneous release). Cytotoxicity was calculated using the following formula:

Percentage cytotoxicity=[(experimental absorbance—spontaneous release of effector cells)—spontaneous release of targets cells/(maximal release—spontaneous release of target cells)×100.

Immunization of Mice with Peptide-Pulsed DC

Day 7 bone marrow-derived DCs were transfected with IDO-siRNA, or transfection reagent alone as described above, and pulsed with 10 µg/ml of keyhole limpet hemocyanin (KLH) (Sigma-Aldrich Rockford Ill.) antigen for 24 h. DCs were then activated with LPS+TNFα for 24 h, washed extensively and used for subsequent transfer experiments. Antigen-pulsed DCs ($2\times10^6$ cells/mouse) were injected subcutaneously into syngeneic mice. Mice were sacrificed after 10 days and cell suspensions were prepared from the draining lymph nodes. These cells were cultured in 96-well plates at a concentration of $4\times10^5$ cells/well in the presence or absence of antigen for 72 h. Cells were pulsed with 1 µCl [$^3$H]-thymidine for the last 18 h. The cultures were harvested onto glass fiber filters (Wallac, Turku, Finland). Radioactivity was counted using a Wallac 1450 Microbeta liquid scintillation counter and the data was analyzed with UltraTerm 3 software.

Mixed Leukocyte Reaction (MLR)

Transfected DCs were plated at a concentration of $1\times10^6$ cells/well in 24-well plates and stimulated with LPS (10 ng/ml, Sigma Aldrich, St Louis, Mo.)+TNF-α (10 ng/ml, Peprotech) for 48 h, at which point supernatant was extracted and used for an ELISA and RNA was extracted from the cells for RT-PCR analysis. For the mixed leukocyte reaction (MLR), T cells were purified from BALB/c splenocytes using nylon wool columns and were used as responders ($1\times10^6$/well). siRNA-treated DCs ($5-40\times10^3$, C57/BL6 origin) were used as the stimulators. A 72 h MLR was performed and the cells were pulsed with 1 µCl [$^3$H]-thymidine for the last 18 h. The cultures were harvested onto glass fiber filters (Wallac, Turku, Finland). Radioactivity was counted using a Wallac 1450 Microbeta liquid scintillation counter and the data was analyzed using UltraTerm 3 software.

Animal Experiments

B16 cells were transfected with IDO-siRNA. Twenty four hours after transfection, the cells were harvested and washed twice in PBS and the number of viable cells was counted by trypan blue exclusion. $2\times10^5$ cells in a volume of 0.2 ml PBS were injected S.C. into the upper hind flanks of each mouse. Mice were checked every other day. When tumors appeared, the tumor size was measured with a caliper and the volumes were calculated by the following formula: tumor volume=0.5×the smallest diameter$^2$×the largest diameter.

For in vivo treatment, $2\times10^5$ cells were suspended in 200 µl of PBS and injected subcutaneously into the upper hind flanks of each mouse. When the tumor size reached about 5 to 7 mm in diameter, six mice in each group received the first intratumoral or systemic injection of siRNA.

Statistics

Survival of tumor-bearing mice was compared among experimental groups using the rank-log test. The unpaired student t test, assuming equal variances, was used to determine the statistical significance of the difference in mean cell number or mean percentage in flow cytometry. This test was also used analyzing data when two groups were compared. MLR data was analyzed using a One-way ANOVA followed by the Newman Keuls Test. Differences with ρ-values less than 0.05 were considered significant.

Example 2

IDO is Efficiently Silenced by siRNA in B16 Melanoma Cells

IDO has been demonstrated to be expressed in B16 melanomas. To test the efficacy of gene silencing in the B16 melanoma cell line, a liposome transfection method was incorporated to deliver our IDO-siRNA-containing pQuiet plasmid into B16 cells in vitro. Twenty four hours after transfection, potent gene silence was observed at the transcriptional level as detected by RT-PCR (FIG. 1A). The protein level of IDO was also significantly decreased as detected by Western Blotting (FIG. 1B), suggesting the expression of IDO in B16 cells could be effectively inhibited by IDO-siRNA.

Since IDO functions as a specific enzyme to primarily catabolize tryptophan, in order to characterize the effects of silencing on enzyme efficacy the change in levels of tryptophan in B16 culture medium upon silencing was detected. B16 cells silenced by siRNA displayed significantly lower IDO functionality (p<0.05) than B16 cells transfected with non-specific siRNA. This was indicated by higher levels of tryptophan (FIG. 1C) and lower levels of kynurenine (FIG. 1D) in the medium of silenced cells in comparison with the medium of nonsense-siRNA-treated B16 cells, the negative control, as detected by High Performance Liquid Chromatography (HPLC). The medium of silenced cells displayed similar tryptophan (FIG. 1C) and kynurenine (FIG. 1D) levels as the positive control which contained pure complete medium and was used to establish baseline tryptophan and kynurenine levels. Taken together, these data suggest that IDO enzyme function was efficiently reduced by siRNA-based silencing.

Example 3

Silencing IDO in B16 Cells Prior to Inoculation Inhibits Tumor Growth

It has been reported that IDO expression is correlated with tumor progression. Tumor cells expressing IDO produce larger and more aggressive tumors than those which have been chemically silenced of IDO expression (4). It was therefore postulated that siRNA-induced silencing of IDO in B16 cells prior to inoculation would restrain tumor growth substantially. To test this hypothesis, IDO-siRNA into B16 cells were transfected using a liposome transfection method in vitro. IDO-silenced B16 cells were then subcutaneously injected in to syngeneic C57/BL6 mice. As demonstrated in FIG. 2A, tumor onset time in IDO-siRNA-treated mice was substantially postponed (p<0.0001) in comparison with mice injected with non-silenced or nonsense-siRNA-treated B16 cells.

Figure 2:
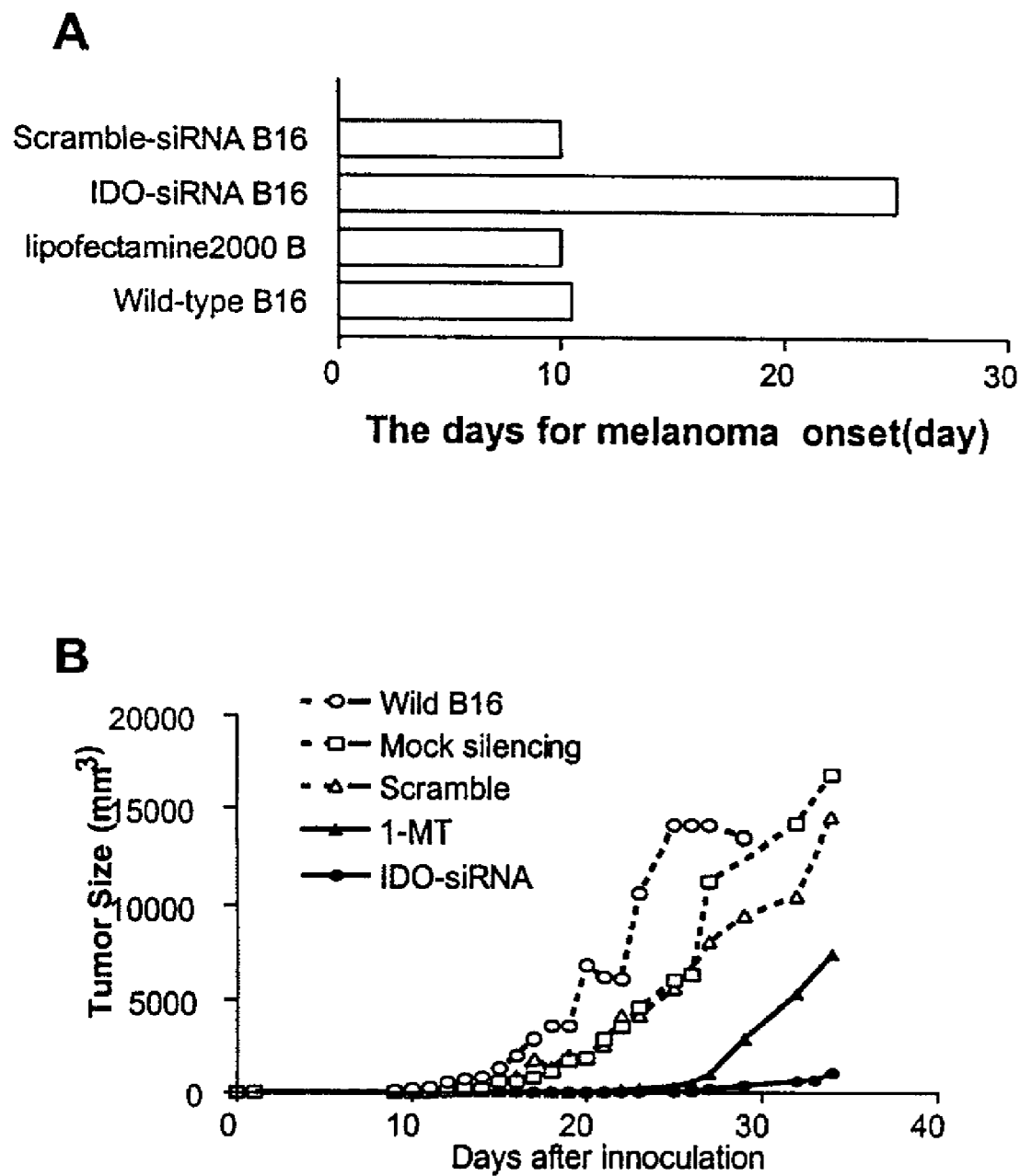
FIGS. 2A and 2B demonstrate that silencing IDO in B16 cells prior to challenge hinders tumor progression and tumor onset.

In addition to tumor onset time, also observed were the sizes of tumors derived from IDO-silenced and control B16 cells. Wild-type B16 cells, as well as mock-silenced (reagent alone) and nonsense-siRNA-treated B16 cells, grew vigorously in syngeneic C57/BL6 mice. While treatment with 1-MT, an IDO chemical inhibitor, only partially inhibited tumor growth, IDO-siRNA treatment of B16 cells prior to subcutaneous challenge led to a remarkable suppression in tumor growth resulting in tumors roughly 15 times smaller than all negative controls 34 days post challenge (FIG. 2B).

Example 4

Silencing IDO in B16 Cells Suppresses Tumor-Induced T Cell Apoptosis

Figure 3:
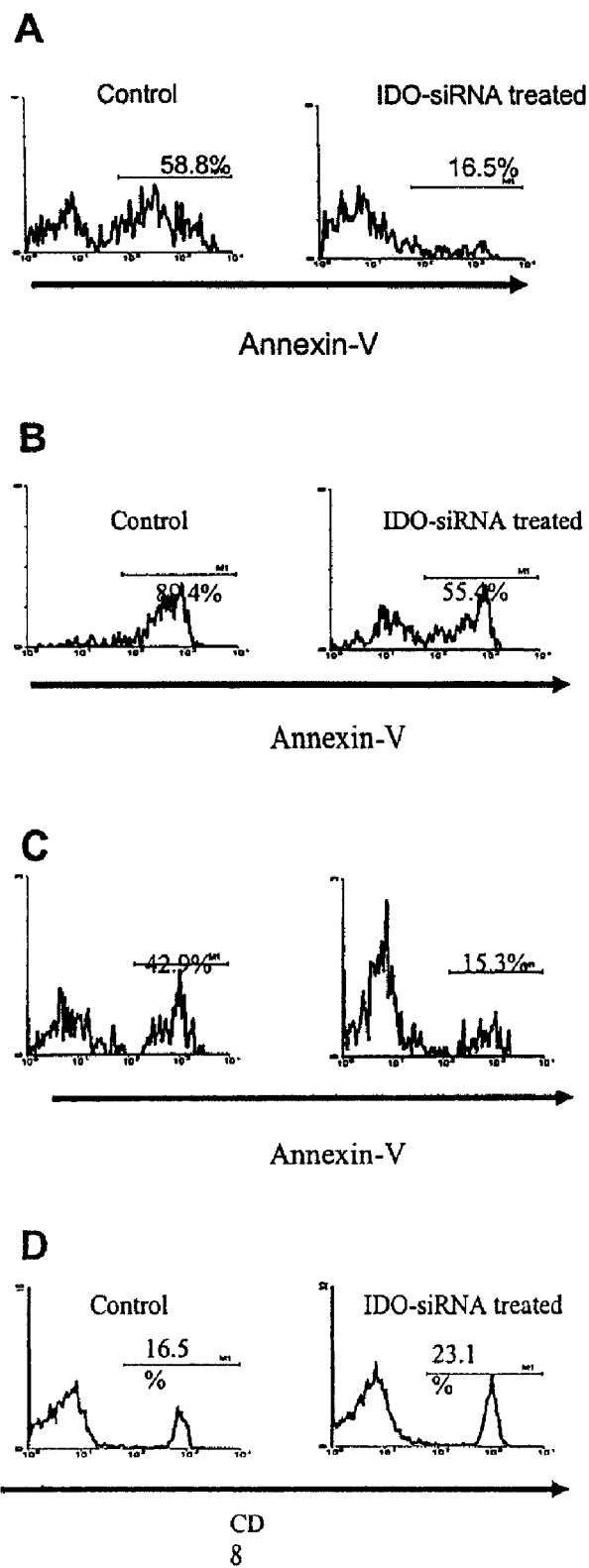
FIGS. 3A through 3D demonstrate that silencing IDO suppresses B16-induced T cell apoptosis.

As indicated earlier, IDO is believed to substantially inhibit T cells most likely due to T cells' extreme sensitivity to local tryptophan levels (4, 9) and to downstream metabolites of the kynurenine pathway (8, 28). It is therefore believed that IDO inhibition occurs through two distinct mechanisms, one targeting the proliferation of locally responding T cells, while the other inducing apoptosis of them. It was therefore hypothesized that silencing IDO using siRNA would reduce tumor-induced T cell apoptosis. Initially a much smaller proportion of T cells undergoing apoptosis in B/6 mice receiving intra-tumoral IDO-siRNA treatment (FIG. 3A) was observed. T cell apoptosis in vitro was characterized and it was observed that B16 cells induced widespread apoptosis in both CD4+ (FIG. 3B) and CD 8+ T cells (FIG. 3C) as detected by FITC-conjugated Annexin-V staining and subsequent FACS analysis. As was expected, the silencing of IDO led to a significant reduction in apoptosis in both subsets of T cells, but most prominently in CD8+ T cells (34.0% vs. 27.6%; difference in proportion of apoptosized Annexin-V-stained cells detected between control and experimental in CD8+ T cells vs. CD4+ T cells). These observations led to the postulation that decreasing the ratio of CD8+ T cells (the primary anti-tumor effector) through tumor-induced apoptosis represented a means of tumor evasion and can be subsequently reversed by IDO-siRNA treatment. In support of this notion, it was found that the overall proportion of CD8+ T cells was higher in mice treated intra-tumorally with IDO-siRNA (16.5% vs 23.1) in comparison with untreated control mice (FIG. 3D).

Example 5

Treating Melanoma by in vivo IDO-siRNA Administration

Figure 4:
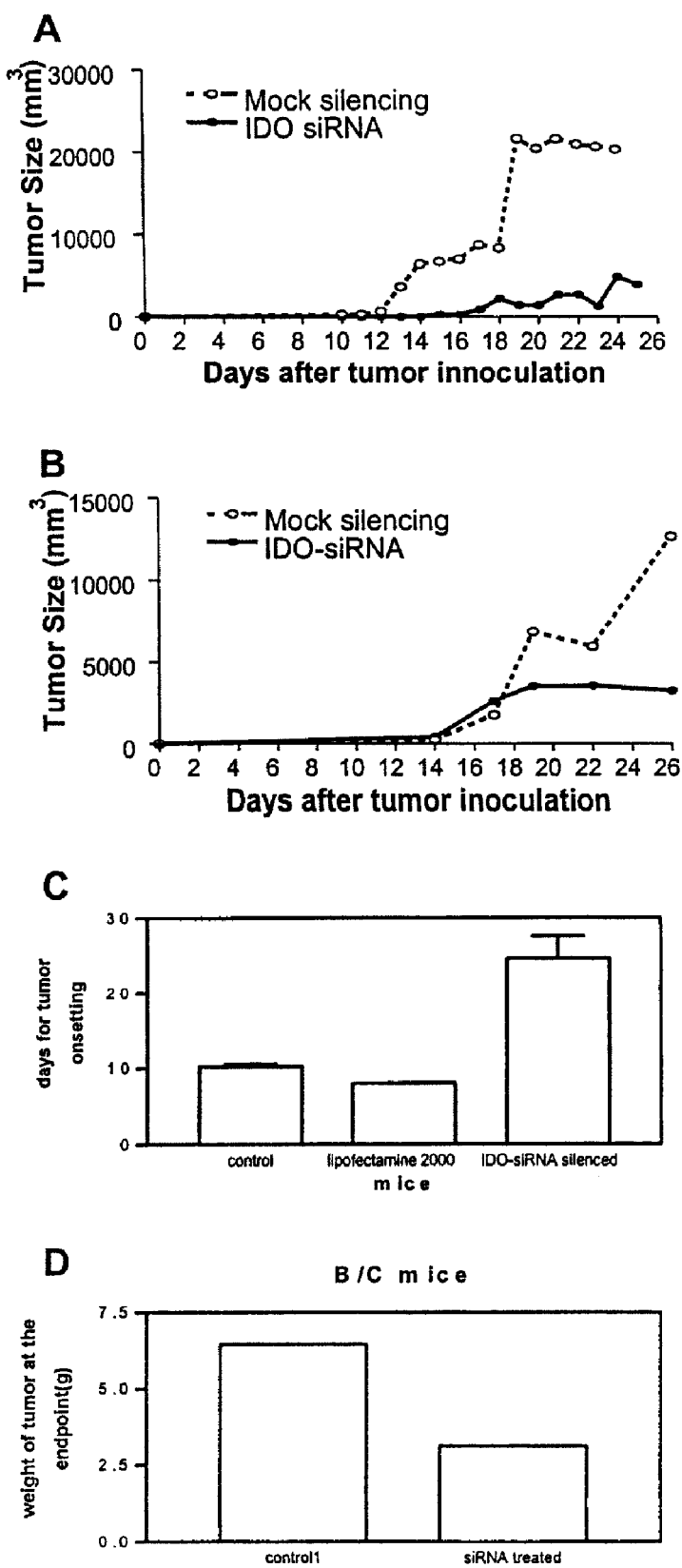
FIGS. 4A through 4D demonstrate that intra-tumor IDO-siRNA-based treatment of melanoma inhibits tumor growth in B/6 and Balb/C mice.

Suppression of IDO using the chemical antagonist 1-MT has been reported to restrain tumor growth in the P815 murine mastocytoma model (4). The feasibility of intra-tumoral treatment of melanoma using IDO-siRNA was demonstrated. A melanoma cell line was established by injecting B16 cells into the hind flanks of syngeneic recipient C57/BL6 mice. 50 µg of IDO-siRNA, introduced by liposomes, were injected intra-tumorally into tumor-bearing recipients three times when tumor size had reached 5 to 7 mm in diameter. Intra-tumor IDO-siRNA treatment significantly restrained tumor growth in comparison with non-treated mice (transfection reagent alone, FIG. 4A). Similar results were observed in allogeneic recipient BALB/c mice (FIG. 4B).

The in vivo administration of IDO-siRNA not only postponed the onset of tumor formation, but also dramatically decreased tumor sizes in syngeneic C57/BL6 (FIG. 4C) and BALB/c (FIG. 4D) recipients respectively. These results implied a novel anti-cancer therapy through inhibition tumor-derived immune suppressive molecule IDO using siRNA.

Example 6

Reinstalling Anti-Tumor Immunity Through Targeted Silencing of IDO

The mechanisms responsible for the immunosuppressive actions of IDO have been proposed to be two-fold, functioning through either: 1) depletion of tryptophan (4, 9) and/or 2) generation of toxic downstream metabolites of the kynurenine cascade including picolinic and quinolinic acids (27-29). Both of these activities may suppress the T cell response through a decrease in proliferation and effector function or alternatively through the induction of apoptosis (more pertinent to the latter mechanism). In order to recover tumor immunity it is necessary to disrupt this mechanism of immunosuppression and prevent evasion. Based on the potential of IDO-siRNA treatment from the previous in vitro and in vivo experiments disclosed herein it was proposed that siRNA-derived treatment could rescue the immune response allowing for recovery of a potent and directed anti-tumor immune response driven primarily by cytotoxic T lymphocytes.

Figure 5:
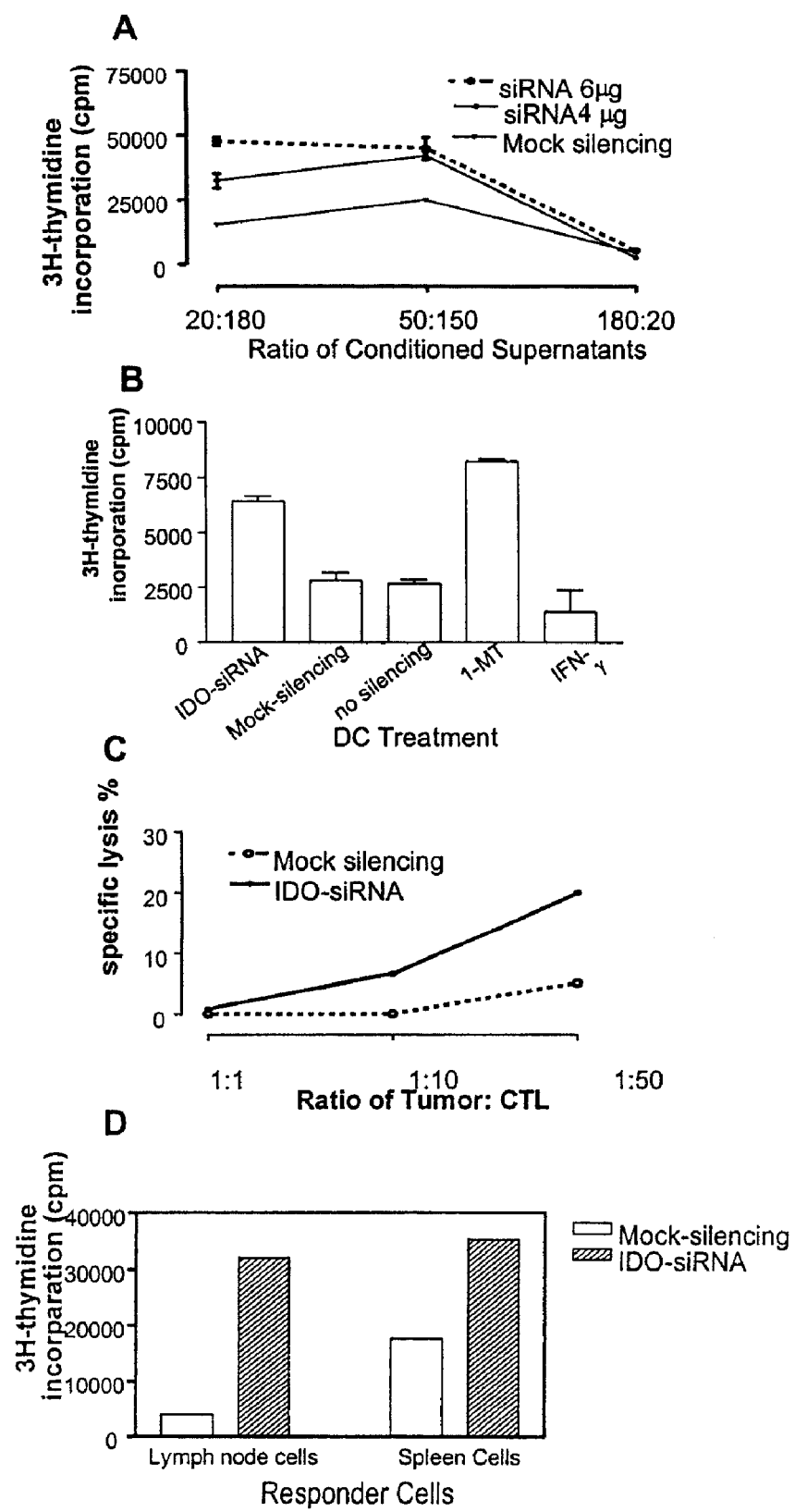
FIGS. 5A through 5D demonstrate rescue of anti-tumor immunity by treatment with IDO-siRNA.

Since tryptophan reduction has been implemented in subsequent suppression of T cell suppression (4, 9), the anti-proliferative effects imposed by B16 culture supernatant which was previously shown to exhibit substantially reduced tryptophan levels (FIG. 1C) was examined. As expected, through a [$^3$H] thymidine incorporation assay it was observed that cultural supernatant from IDO-siRNA-treated B16 cells substantially reduced suppression of T cell proliferation when cells were stimulated by anti-CD3 mAb in comparison with supernatant obtained from mock-silenced B16 cells (FIG. 5A). Also, this pattern appeared to be dose-dependant although a larger distribution of doses would be required to fully support this notion (FIG. 5A).

To confirm that the inhibitory effect imposed by the supernatant of B16 cells is related primarily to the expression of IDO, a MLR was performed in which allogeneic BALB/c T cells were co-cultured with C57/BL6 derived DCs that were made to express various levels of IDO through transfection (FIG. 5B). After silencing IDO in DCs using siRNA, T cell proliferation was significantly elevated in comparison to the proliferation observed when non-silenced or mock-silenced DCs were used as stimulators. This enhanced T cell response was also seen in a MLR using DCs in which IDO was inhibited by 1-MT providing further confirmation. On the other hand, when using DCs in which IDO expression was up-regulated by IFN-γ treatment, T cell proliferation was even lower than was observed when using other negative controls (FIG. 5B). IFN-γ is a known stimulator of IDO expression as has been proven in the past (6). Taken in its entirety, the data suggests a very strong mechanistic link between IDO alone and T cell suppression, one which can be subsequently overcome by targeted silencing of IDO.

Since the silencing of IDO led to substantial reduction in both tumor-induced T cell apoptosis (FIG. 3) and in the suppression of T cell proliferation (FIG. 5A), it was further examined whether this recovery of immune response could lead to a subsequent rescue of directed tumor lysis. To achieve this, CD8+ T cells were isolated from B16 tumor-bearing C57/BL mice), and these cells co-cultured with B16 cells either silenced by IDO-siRNA or non-silenced. As shown in FIG. 5C, tumor-specific lysis was significantly enhanced when T cells had been co-cultured with IDO-silenced B16 cells, indicating that IDO plays a critical role in the evasion of targeted CTL-derived lysis, a mechanism which can be enhanced through siRNA-based treatment.

Although tumor-derived expression of IDO has been a characterized mechanism of evasion, the notion of APC-derived immunosuppression through IDO expression has been only weakly explored and remains poorly understood. Based on the present data which indicated that the silencing of IDO in DCs stimulated an increase in T cell response (FIG. 5B), it was postulated that IDO may also disrupt antigen presenting function, a common theme in oncogenesis. To address this, DCs from C57/BL mice were extracted and IDO silenced using siRNA. The DCs were pulsed with KLH, a well-recognized model antigen. After murinal immunization with IDO-silenced or non-silenced DCs, a KLH-specific response assay was performed. As demonstrated in FIG. 5D, IDO-silenced DCs indeed functioned more effectively in antigen presentation than IDO-expressing DCs.

Example 7

Vaccination Using Tumor-Antigen-Pulsed and IDO Silenced Dendritic Cells

Figure 6A:
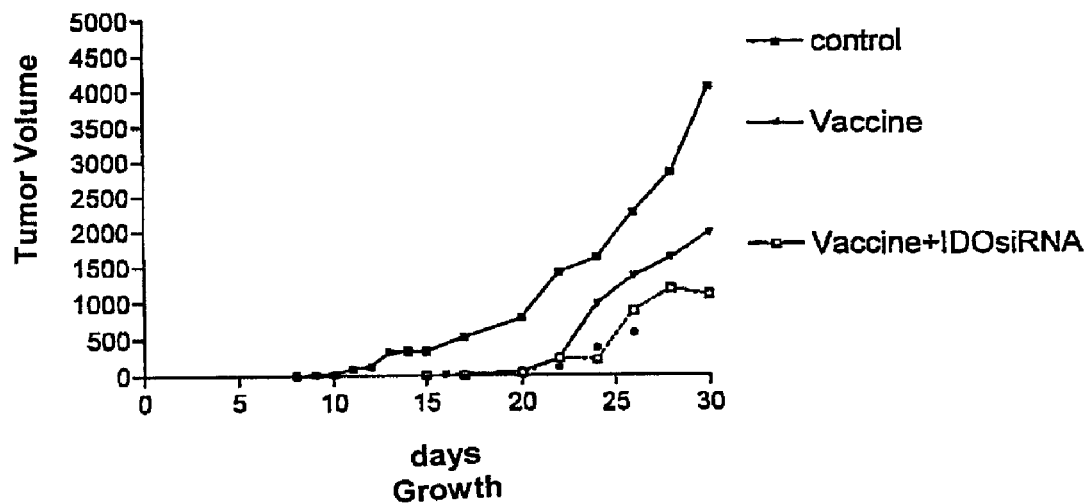
FIG. 6A is a graph demonstrating that the combination of the treatment of the DC vaccine together with the IDO-siRNA significantly decreased tumor volume over time.
Figure 6B:
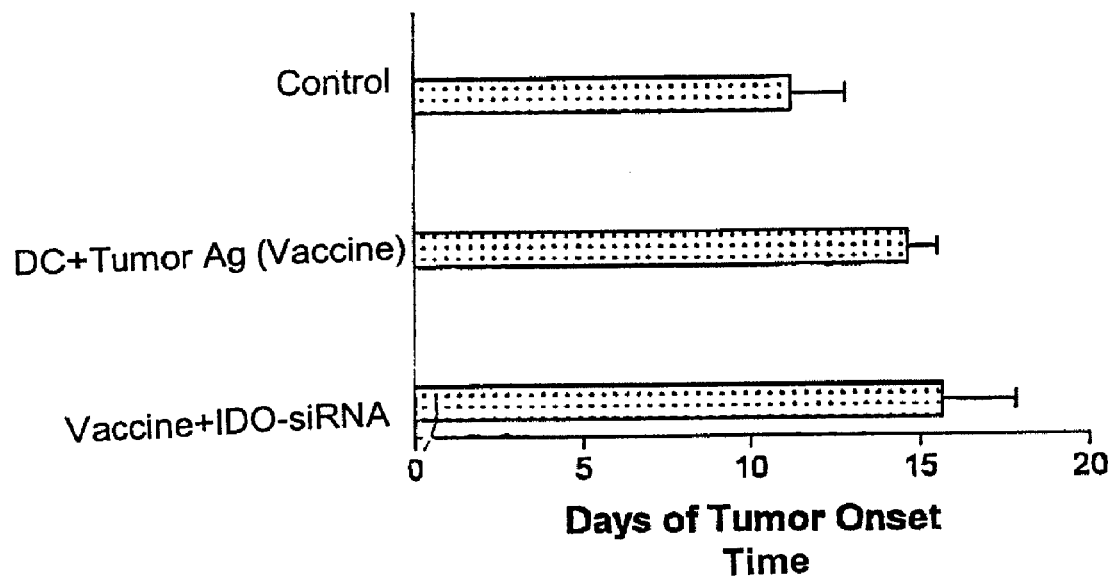
FIG. 6B is a graph demonstrating that the combination of the treatment of the DC vaccine together with the IDO-siRNA increased the days of tumor onset, that is, the development of the tumor was delayed versus control or vaccine alone.
Figure 7:
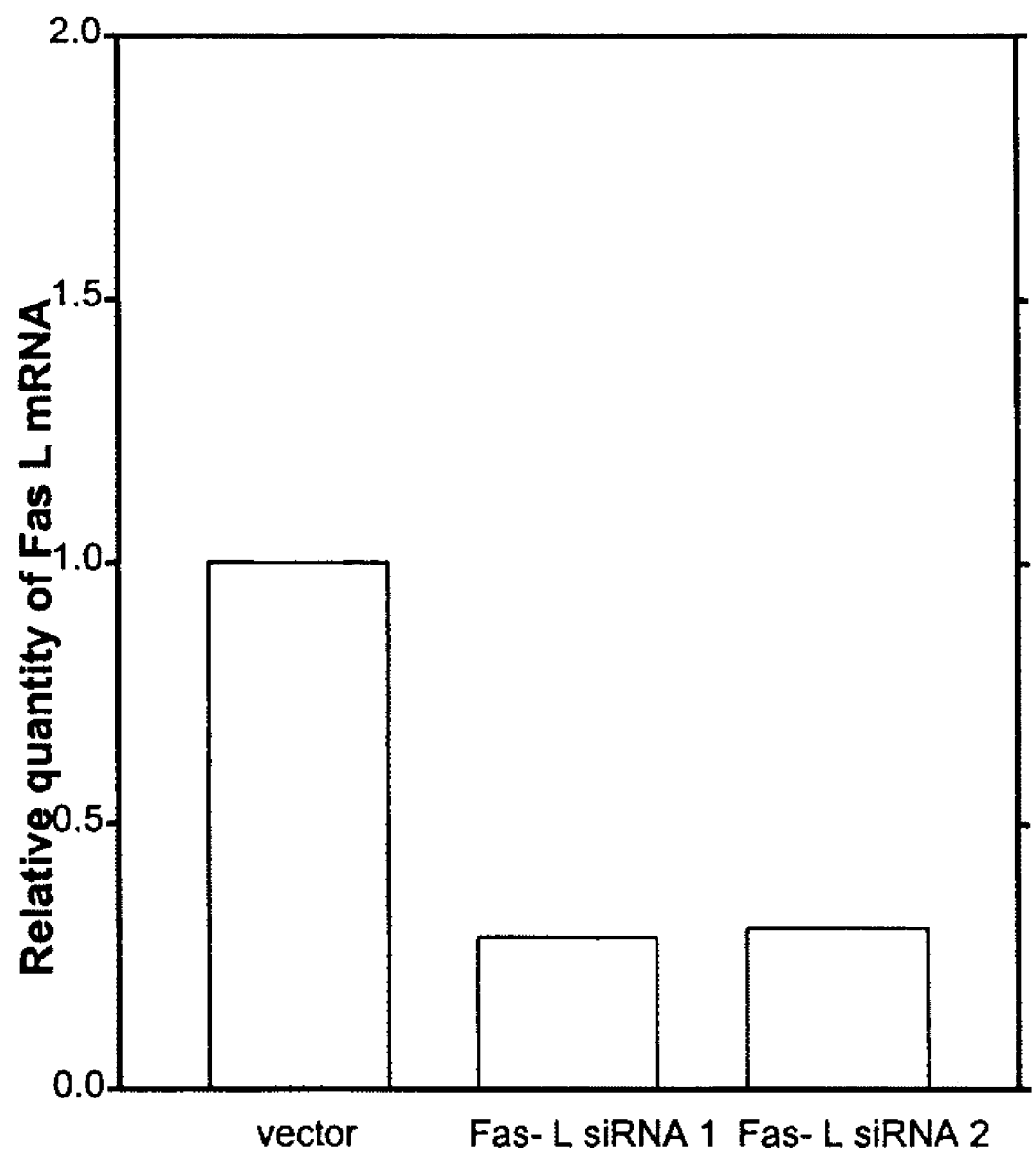
FIG. 7 is a graph showing FasL siRNA gene silencing efficacy.
Figure 8:
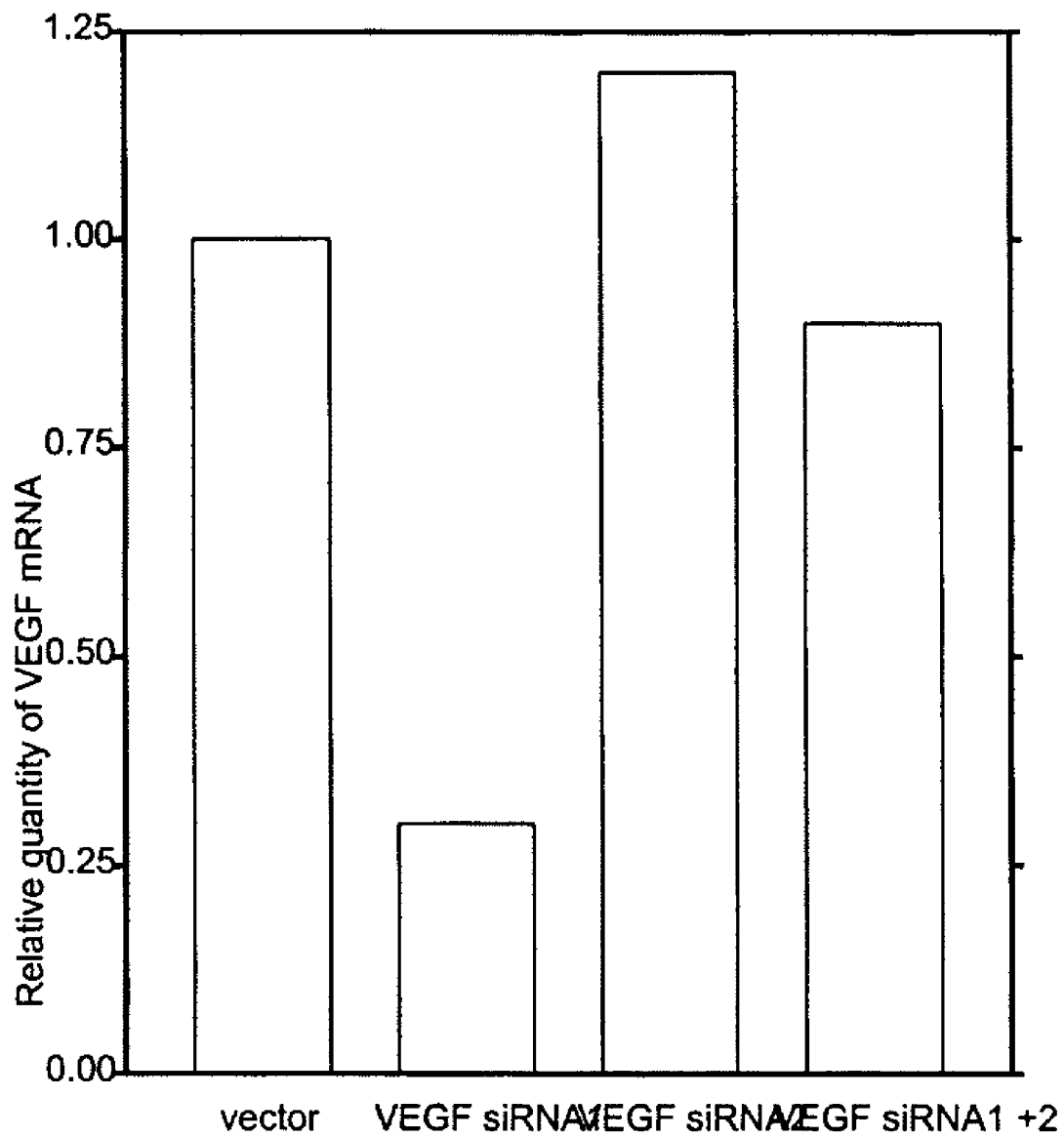
FIG. 8 is a graph showing VEGF siRNA gene silencing efficacy.

Dendritic cells (DC) were cultured from C57BL/6 (B/6) bone marrow progenitors in the presence of murine recombinant GM-CSF (10 ng/ml) and IL-4 (long/ml) in 6-well plate in a volume of 4 ml of complete RPMI 1640. The tumor from a murine melanoma cell line B16 WAS cultured and used for preparing a tumor lysate. 4 µg of tumor lysate was added to each well of DC culture on day 5. After 24 hours culture, DC were be silenced with IDO-siRNA using a liposomal transfection method as discussed supra. On day 8, the tumor-Ag pulsed and IDO silenced DC ($3\times10^6$/mouse) were i.v. injected into B/6 mice. 7 days later, the second immunization was repeated using the same method. The melanoma B16 cells ($2\times10^5$/mouse) were inoculated into B/6 mice 7 days after last immunization. The tumor onset time and tumor size was assessed each day. FIG. 6A is a graph demonstrating that the combination of the treatment of the DC vaccine together with the IDO-siRNA significantly decreased tumor volume over time. FIG. 6B is a graph demonstrating that the combination of the treatment of the DC vaccine together with the IDO-siRNA increased the days of tumor onset, that is, the development of the tumor was delayed versus control or vaccine alone.

Example 8

Preparation of IDO-IL-siRNA

The preparation of immunoliposomes has been described in detail previously by Shi et al [Ningya Shi et al. PNAS. 98:12754]. Liposomes were composed of 18.6 µmol of POPC (1-palmitoyl-2-oleoyl-sn-glycerol-3-phosphocholine), 0.6 µmol DDAB (didodecyldimethylammonium bromide), 0.6 µmol DSPE-PEG2000 (distearoylphosphatidylethanolamine conjugated to a 2000 kDa chain of polyethylene glycol) and 0.2 µmol DSPE-PEG2000-maleimide. Briefly, the lipids were mixed in the appropriate molar ratio and the chloroform solvent is evaporated to leave a thin lipid film coating the interior of the tube. The film was hydrated using 0.05M Tris-HCL (pH 8.0) and sonicated. 500 mg of green fluorescence-labeled siRNA was added to the lipid dispersion, which subsequently, underwent 6 freeze/thaw cycles. The lipid dispersion was diluted using 0.05M HEPES (pH 7.0) and successively extruded through polycarbonate membranes of 400 nm, 200 nm, 100 nm, and 50 nm pore size. Exteriorized siRNA was degraded by exhaustive RNase III digestion, and siRNA-loaded liposomes were purified using a Sepharose CL-4B gel filtration column.

Example 9

Labeling, Thiolation and Conjugation of Anti-MAGE Antibody to IDO-IL-siRNA 1.5 mg of red fluorescence-labeled MAGE-1 IgG (Acris Antibodies Inc, Cat# SP6206), which cross-reacts with both human and mouse MAGE-1, was thiolated and incubated with IDO siRNA-loaded liposomes overnight at room temperature. siRNA-immunoliposomes were purified using a Sepharose CL-4B gel filtration column and column eluates were analyzed by spectrofluorometry. Fractions containing both red and green fluorescence, corresponding to the MAGE-1 antibody and siRNA, respectively, were pooled. These fractions indicate co-migration of siRNA and mAb, suggesting that they are incorporated into the same immunoliposome complex. Finally, the average immunoliposome diameter, 73 nm, was determined by dynamic light scattering.

Although preferred embodiments have been described herein in detail it is understood by those of skill in the art that using no more than routine experimentation, many equivalents to the specific embodiments of the invention described herein can be made. Such equivalents are intended to be encompassed by the scope of the claims appended hereto.

The invention claimed is:

1. A composition comprising an siRNA construct directed to indoleamine 2,3-dioxygenase (IDO) mRNA, said siRNA binding to said IDO, wherein said binding prevents expression of said IDO, thereby modulating IDO-directed tumoral immunosuppression in a mammalian subject and a pharmaceutically acceptable carrier, wherein said siRNA construct is within a liposome coupled to an anti-MAGE antibody that is targeted to a tumor.

2. The composition of claim 1, wherein said composition further comprises a dendritic cell (DC) vaccine comprising one or more tumor antigens.

3. The composition of claim 1, wherein the liposome is an immunoliposome.

4. The composition of claim 1, formulated for intra-tumoral administration.

* * * * *